US008354223B2

(12) United States Patent
Nakamura et al.

(10) Patent No.: US 8,354,223 B2
(45) Date of Patent: Jan. 15, 2013

(54) METHODS OF IDENTIFYING AGENTS THAT MODULATE METHYLATION OF VEGFR1 BY SMYD3

(75) Inventors: Yusuke Nakamura, Tokyo (JP); Yoichi Furukawa, Tokyo (JP); Ryuji Hamamoto, Tokyo (JP); Shuichi Nakatsuru, Kanagawa (JP)

(73) Assignee: Oncotherapy Science, Inc., Kanagawa (JP)

( * ) Notice: Subject to any disclaimer, the term of this patent is extended or adjusted under 35 U.S.C. 154(b) by 217 days.

(21) Appl. No.: 12/664,378

(22) PCT Filed: Jun. 13, 2008

(86) PCT No.: PCT/JP2008/001516
§ 371 (c)(1),
(2), (4) Date: Mar. 31, 2010

(87) PCT Pub. No.: WO2008/152816
PCT Pub. Date: Dec. 18, 2008

(65) Prior Publication Data
US 2010/0184088 A1 Jul. 22, 2010

Related U.S. Application Data

(60) Provisional application No. 60/944,071, filed on Jun. 14, 2007.

(51) Int. Cl.
*C12Q 1/00* (2006.01)
(52) U.S. Cl. .......................................... 435/4
(58) Field of Classification Search ........................ None
See application file for complete search history.

(56) References Cited

U.S. PATENT DOCUMENTS

| 2004/0235018 | A1 | 11/2004 | Nakamura et al. |
| 2009/0035303 | A1 | 2/2009 | Nakamura et al. |
| 2009/0142344 | A1 | 6/2009 | Nakamura et al. |
| 2009/0175844 | A1 | 7/2009 | Nakamura et al. |
| 2009/0191181 | A1 | 7/2009 | Nakamura et al. |
| 2010/0248240 | A1 | 9/2010 | Nakamura et al. |

FOREIGN PATENT DOCUMENTS

| JP | 2004-264294 A | 9/2004 |
| WO | WO 00/17355 A2 | 3/2000 |
| WO | WO 00/44900 A2 | 8/2000 |
| WO | WO 02/059377 A2 | 8/2002 |
| WO | WO 02/090578 A2 | 11/2002 |
| WO | WO 02/092002 A2 | 11/2002 |
| WO | WO 03/010180 A1 | 2/2003 |
| WO | WO 03/027143 A2 | 4/2003 |
| WO | WO 2004/076623 A2 | 9/2004 |
| WO | WO 2005/071102 A2 | 8/2005 |
| WO | WO 2006/085684 A2 | 8/2006 |
| WO | WO 2006/092958 A1 | 9/2006 |
| WO | WO 2007/004526 A2 | 1/2007 |

OTHER PUBLICATIONS

Hamamoto et al teach SMYD3, a methyltransferase (abstract).*
Kunizaki et al , Cancer research, Nov. 2007, 67:10759-10765, IDS.*
Hamamoto et al (Cancer Science, Feb. 2006, 97:113-118, Ids).*
Yamada et al (Cancer Science, 2003, 94:536-539).*
U.S. Appl. No. 13/076,137, filed Mar. 30, 2011, 53 pages.
U.S. Appl. No. 13/092,770, filed Apr. 22, 2011, 59 pages.
U.S. Appl. No. 13/377,110, which is a U.S. National Stage of PCT/JP2010/003871, filed Jun. 10, 2010, 69 pages.
Iwabata, H., et al., "Proteomic analysis of organ-specific post-translational lysine-acetylation and -methylation in mice by use of anti-acetyllysine and -methyllysine mouse monoclonal antibodies," *Proteomics*, vol. 5(18), pp. 4653-4664 (Dec. 2005).
Du, Y., et al., "Hypermethylation in Human Cancers of the RIZ1 Tumor Suppressor Gene, a Member of a Histone/Protein Methyltransferase Superfamily," *Cancer Res.*, vol. 61(22), pp. 8094-8099 (Nov. 15, 2001).
Echeverri, C., et al., "siRNA Design: It's All in the Algorithm," *Ambion TechNotes 11* (Oct. 3. 2004) (http://www.ambion.com/techlib/tn/113/14.html).
Firestein, R., et al., "Set Domain-Dependent Regulation of Transcriptional Silencing and Growth Control by SUV39H1, a Mammalian Ortholog of *Drosophila* Su(var)3-9," *Mol. Cell Biol.*, vol. 20(13), pp. 4900-4909 (Jul. 2000).
Fu, T-B., et al., "The RNAs of Hepatitis Delta Virus are Copies by RNA Polymerase II in Nuclear Homogenates," *J. Virol.*, vol. 67(12), pp. 6965-6972 (Dec. 1993).
Hamamoto, R., et al., "SMYD3 endoes a histone methyltransferase involved in the proliferation of cancer cells," *Nat. Cell Biol.*, vol. 6(8), pp. 731-740 (Aug. 2004), Epub Jul. 4, 2004).
Hamamoto, R., et al., "Isolation and characterization of ZNFN3A1, a novel gene whose expression is frequently up-regulated in hepatocellular carcinoma," *Jpn J Cancer Res (Proceedings of the Sixtieth Annual Meeting of the Japanese Cancer Association)*, vol. 92(Supplement), p. 117, abstract No. 208 (2001).
Hamamoto, R., et al., "ZNDN3A1, a novel gene that promotes cell growth in hepatocellular carcinoma," *Proceedings/Annual Meeting of the American Association for Cancer Research/Annual Meeting of the American Society of Clinical Oncology, American Association for Cancer Research*, Meeting (43), 13-13 (Mar. 1, 2002).
Hamamoto, R., et al., "Enhanced SMYD3 expression is essential for the growth of breast cancer cells," *Cancer Sci.*, vol. 97(2), pp. 113-118 (Feb. 2006).
Keto, T., et al., "Isolation of a novel human gene, DDELF1 (Development and Differentiation Enhancing Factor-Like 1)," *Jpn J Cancer Res (Proceedings Sixty-First Annual Meeting of the Japanese Cancer Association*, vol. 93(Supplement), p. 78, abstract No. 2033 (2002).
Kunizaki, M., et al., "The Lysine 831 of Vascular Endothelial Growth Factor Receptor 1 is a Novel Target of Methylation by SMYD3," *Cancer Res.*, vol. 67(22), pp. 10759-10765 (Nov. 15, 2007).

(Continued)

*Primary Examiner* — Laura B Goddard
(74) *Attorney, Agent, or Firm* — Kilpatrick Townsend & Stockton LLP

(57) ABSTRACT

The present invention relates to methods for determining the methyltransferase activity of a polypeptide and screening for modulators of methyltransferase activity, more particularly for modulators of the methylation of VEGFR1 by SMYD3. The invention further provides methods and pharmaceutical compositions for treating and preventing colorectal cancer, hepatocellular carcinoma, bladder cancer and/or breast cancer using a modulator so identified.

3 Claims, 4 Drawing Sheets

OTHER PUBLICATIONS

Luking, A., et al., "The Protein Family of RNA Helicases," *Crit. Rev. Biochem. Mol. Biol.*, vol. 33(4), pp. 259-296 (1998).

Nakajima, T., et al., "RNA Helicase a Mediates Association of CBP with RNA Polymerase II," *Cell*, vol. 90(6), pp. 1107-1112 (Sep. 19, 1997).

Nozaki, K., et al., "Involvement of the VEGFR-1 in prostatic carcinogenesis," *Proceedings of the American Association for Cancer Research*, vol. 45, p. 213, abstract No. 934 (2004).

Okabe, H., et al., "Genome-wide Analysis of Gene Expression in Human Hepatocellular Carcinomas Using cDNA Microarray: Identification of Genes Involved in Viral Carcinogenesis and Tumor Progression," *Cancer Res.*, vol. 61(5), pp. 2129-2137 (Mar. 1, 2001).

Rea, S., et al., "Regulation of chromatin structure by site-specific histone H3 methyltransferases," *Nature*, vol. 406(6796), pp. 593-599 (Aug. 10, 2000).

Rozovskaia, T., et al., "Self-association of the SET domains of human ALL-1 and of *Drosophila* Trithorax and ASH1 proteins," *Oncogene*, vol. 19(3), pp. 351-357 (Jan. 20, 2000).

Shibuya, M., "Differential Roles of Vascular Endothelial Growth Factor Receptor-1 and Receptor-2 in Angiogenesis," *J. Biochem. Mol. Biol.*, vol. 39(5), pp. 469-478 (Sep. 30, 2006).

Stockand, J., et al., "S-Adenosyl-L-homocysteine Hydrolase Regulates Aldosterone-induced $Na^+$ Transport," *J. Biol. Chem.*, vol. 274(6), pp. 3842-3850 (Feb. 5, 1999).

Strahl, B., et al., "Methylation of histone H3 at lysine 4 is highly conserved and correlates with transcriptionally active nuclei in *Tetrahymena*," *Proc. Nat'l Acad. Sci. USA*, vol. 96(26), pp. 14967-14972 (Dec. 21, 1999).

Strausberg, R., et al., "Generation and initial analysis of more than 15,000 full-length human and mouse cDNA sequences," *Proc. Nat'l Acad. Sci USA*, vol. 99(26), pp. 16899-16903 (Dec. 24, 2002, Epub Dec. 11, 2002).

Tsuge, M., et al., "A variable number of tandem repeats polymorphism in an E2F-1 binding element in the 5' flanking region of SMYD2 is a risk factor for human cancers," *Nat. Genet.*, vol. 37(10), pp. 1104-1107 (Oct. 2005, Epub Sep. 11, 2005).

GENESEQ Accession No. AAG66728, 1 pg (Nov. 26, 2001).
GENBANK Accession No. BC031010, 3 pgs. (Jun. 13, 2002).
EMBL Accession No. AK024733, 2 pgs. (Sep. 29, 2000).
EMBL Accession No. AL557360, 2 pgs. (Feb. 11, 2001).
GENECARDS Accession No. GC01M242239, 8 pgs. (Jan. 1, 2004).
U.S. Appl. No. 13/403,623, filed Feb. 23, 2012, 95 pgs.
U.S. Appl. No. 13/536,327, filed Jun. 28, 2012, 204 pgs.
U.S. Appl. No. 13/168,720, 206 pages, filed Jun. 24, 2011.

* cited by examiner

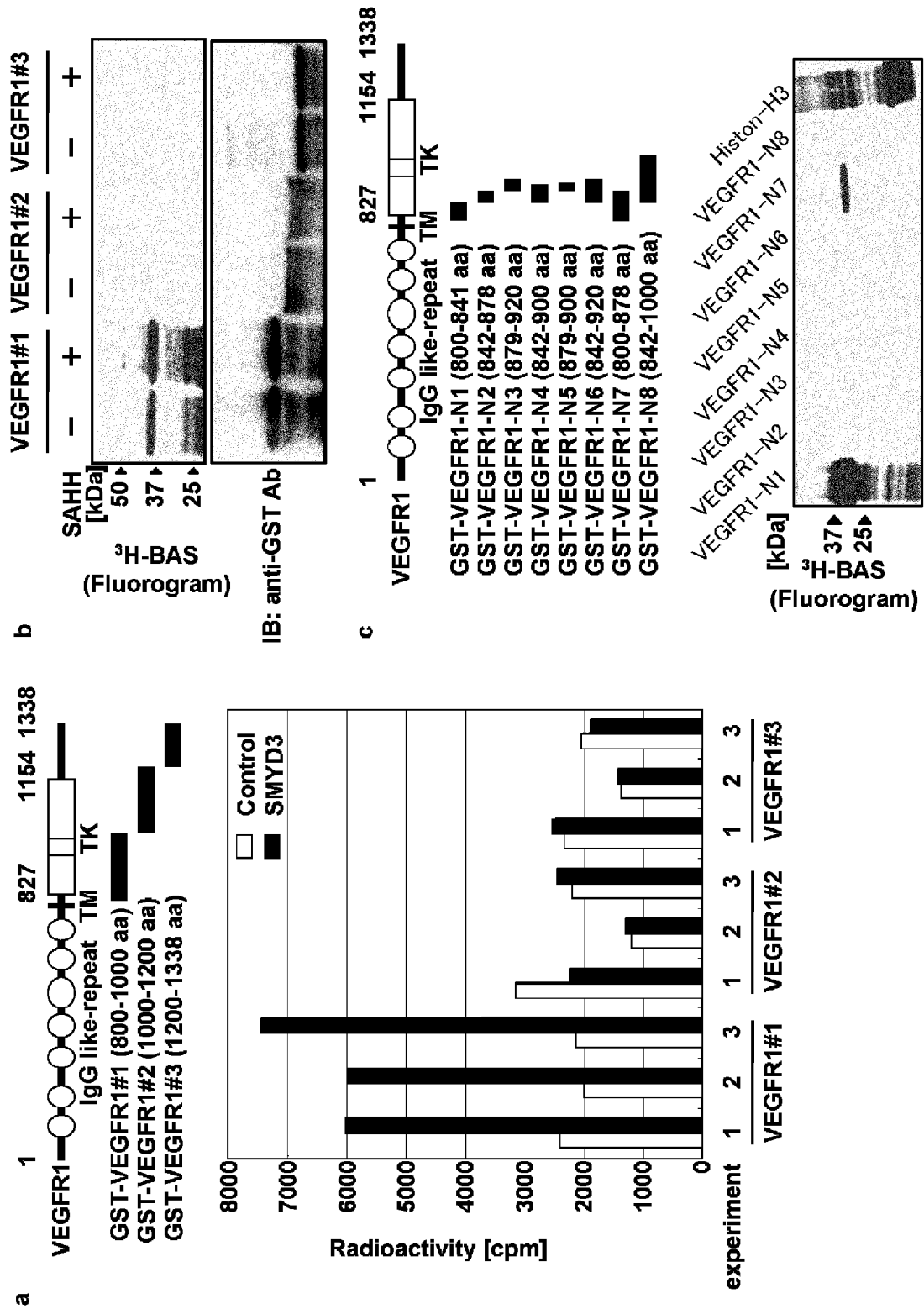
[Fig. 1]

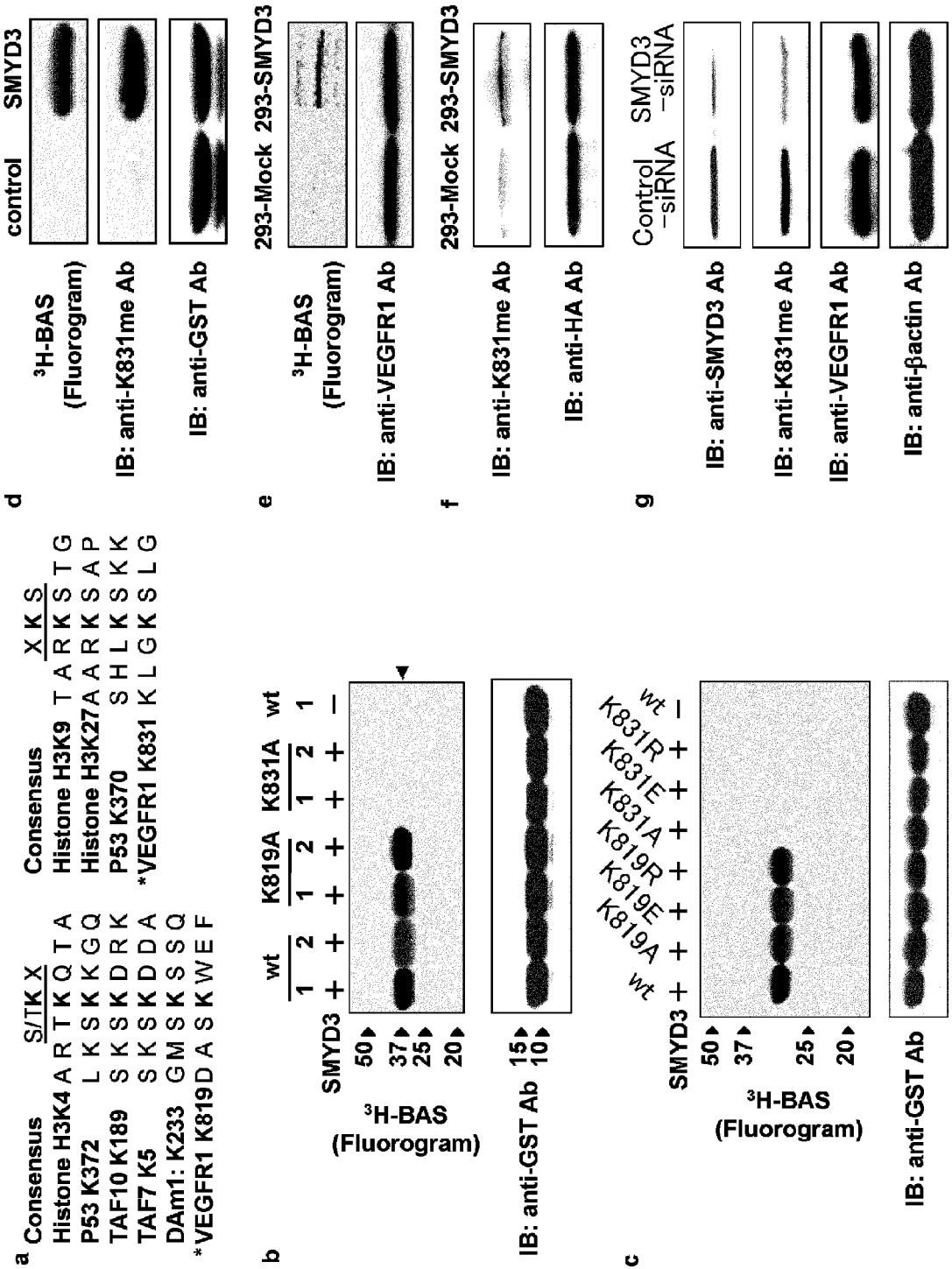

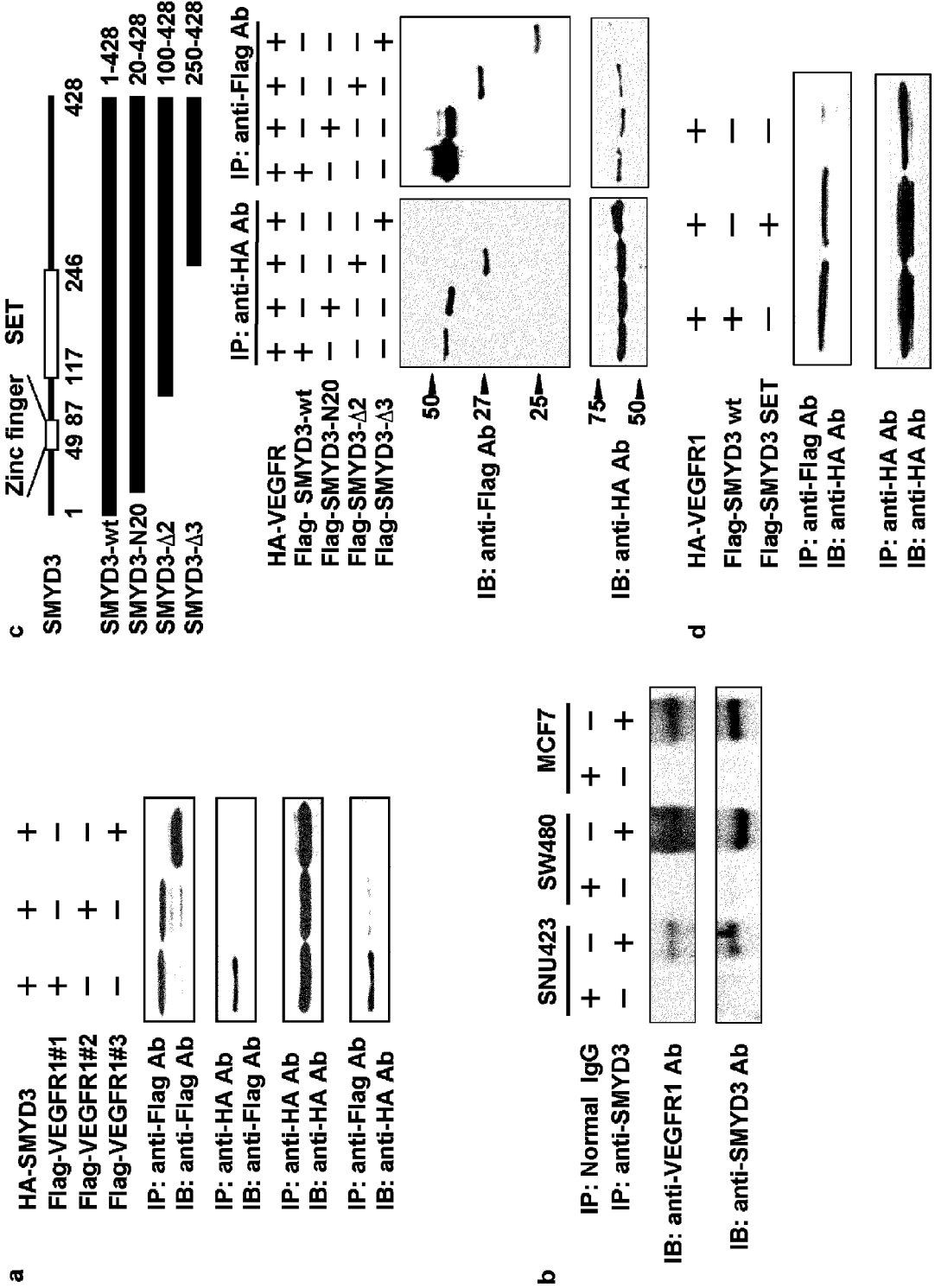

[Fig. 4]
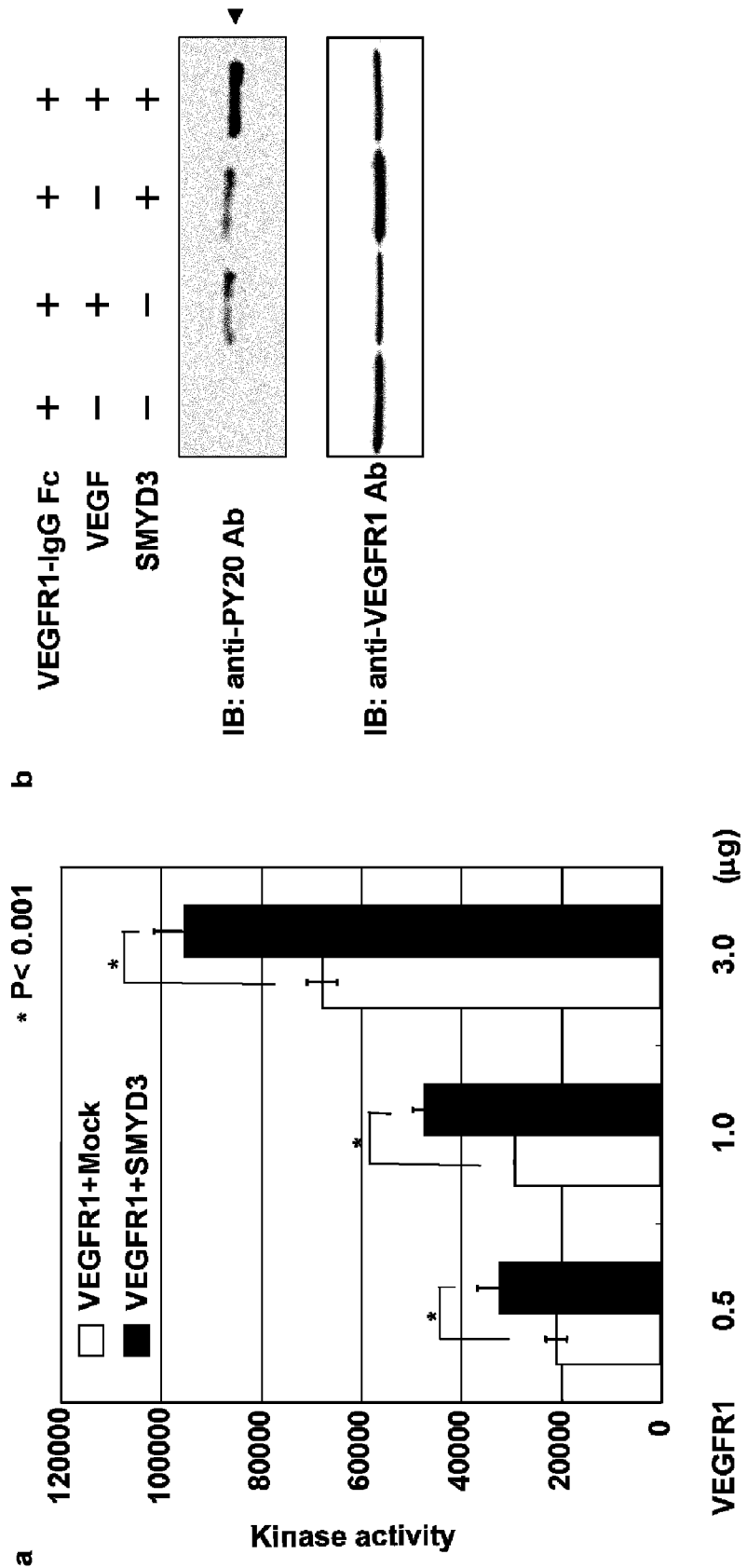

SEQUENCE LISTING

```
<160> NUMBER OF SEQ ID NOS: 39

<210> SEQ ID NO 1
<211> LENGTH: 1622
<212> TYPE: DNA
<213> ORGANISM: Homo sapiens
<220> FEATURE:
<221> NAME/KEY: CDS
<222> LOCATION: (96)..(1382)

<400> SEQUENCE: 1
gtgcgcgcag ggcgcaggcg cgcgggtccc ggcagcccgt gagacgcccg ctgctggacg         60
cgggtagccg tctgaggtgc cggagctgcg ggagg atg gag ccg ctg aag gtg         113
                                      Met Glu Pro Leu Lys Val
                                        1               5 gaa aag ttc gca acc gcc aac agg gga aac ggg ctg cgc gcc gtg acc         161
Glu Lys Phe Ala Thr Ala Asn Arg Gly Asn Gly Leu Arg Ala Val Thr
             10                  15                  20 ccg ctg cgc ccc gga gag cta ctc ttc cgc tcg gat ccc ttg gcg tac         209
Pro Leu Arg Pro Gly Glu Leu Leu Phe Arg Ser Asp Pro Leu Ala Tyr
         25                  30                  35 acg gtg tgc aag ggg agt cgt ggc gtc gtc tgc gac cgc tgc ctt ctc         257
Thr Val Cys Lys Gly Ser Arg Gly Val Val Cys Asp Arg Cys Leu Leu
     40                  45                  50 ggg aag gaa aag ctg atg cga tgc tct cag tgc cgc gtc gcc aaa tac         305
Gly Lys Glu Lys Leu Met Arg Cys Ser Gln Cys Arg Val Ala Lys Tyr
 55                  60                  65                  70
```

```
tgt agt gct aag tgt cag aaa aaa gct tgg cca gac cac aag cgg gaa    353
Cys Ser Ala Lys Cys Gln Lys Lys Ala Trp Pro Asp His Lys Arg Glu
            75                  80                  85 tgc aaa tgc ctt aaa agc tgc aaa ccc aga tat cct cca gac tcc gtt    401
Cys Lys Cys Leu Lys Ser Cys Lys Pro Arg Tyr Pro Pro Asp Ser Val
            90                  95                 100 cga ctt ctt ggc aga gtt gtc ttc aaa ctt atg gat gga gca cct tca    449
Arg Leu Leu Gly Arg Val Val Phe Lys Leu Met Asp Gly Ala Pro Ser
           105                 110                 115 gaa tca gag aag ctt tac tca ttt tat gat ctg gag tca aat att aac    497
Glu Ser Glu Lys Leu Tyr Ser Phe Tyr Asp Leu Glu Ser Asn Ile Asn
        120                 125                 130 aaa ctg act gaa gat aag aaa gag ggc ctc agg caa ctc gta atg aca    545
Lys Leu Thr Glu Asp Lys Lys Glu Gly Leu Arg Gln Leu Val Met Thr
135                 140                 145                 150 ttt caa cat ttc atg aga gaa gaa ata cag gat gcc tct cag ctg cca    593
Phe Gln His Phe Met Arg Glu Glu Ile Gln Asp Ala Ser Gln Leu Pro
                155                 160                 165 cct gcc ttt gac ctt ttt gaa gcc ttt gca aaa gtg atc tgc aac tct    641
Pro Ala Phe Asp Leu Phe Glu Ala Phe Ala Lys Val Ile Cys Asn Ser
            170                 175                 180 ttc acc atc tgt aat gcg gag atg cag gaa gtt ggt gtt ggc cta tat    689
Phe Thr Ile Cys Asn Ala Glu Met Gln Glu Val Gly Val Gly Leu Tyr
            185                 190                 195 ccc agt atc tct ttg ctc aat cac agc tgt gac ccc aac tgt tcg att    737
Pro Ser Ile Ser Leu Leu Asn His Ser Cys Asp Pro Asn Cys Ser Ile
        200                 205                 210 gtg ttc aat ggg ccc cac ctc tta ctg cga gca gtc cga gac atc gag    785
Val Phe Asn Gly Pro His Leu Leu Leu Arg Ala Val Arg Asp Ile Glu
215                 220                 225                 230 gtg gga gag gag ctc acc atc tgc tac ctg gat atg ctg atg acc agt    833
Val Gly Glu Glu Leu Thr Ile Cys Tyr Leu Asp Met Leu Met Thr Ser
                235                 240                 245 gag gag cgc cgg aag cag ctg agg gac cag tac tgc ttt gaa tgt gac    881
Glu Glu Arg Arg Lys Gln Leu Arg Asp Gln Tyr Cys Phe Glu Cys Asp
            250                 255                 260 tgt ttc cgt tgc caa acc cag gac aag gat gct gat atg cta act ggt    929
Cys Phe Arg Cys Gln Thr Gln Asp Lys Asp Ala Asp Met Leu Thr Gly
            265                 270                 275 gat gag caa gta tgg aag gaa gtt caa gaa tcc ctg aaa aaa att gaa    977
Asp Glu Gln Val Trp Lys Glu Val Gln Glu Ser Leu Lys Lys Ile Glu
        280                 285                 290 gaa ctg aag gca cac tgg aag tgg gag cag gtt ctg gcc atg tgc cag   1025
Glu Leu Lys Ala His Trp Lys Trp Glu Gln Val Leu Ala Met Cys Gln
295                 300                 305                 310 gca atc ata agc agc aat tct gaa cgg ctt ccc gat atc aac atc tac   1073
Ala Ile Ile Ser Ser Asn Ser Glu Arg Leu Pro Asp Ile Asn Ile Tyr
                315                 320                 325 cag ctg aag gtg ctc gac tgc gcc atg gat gcc tgc atc aac ctc ggc   1121
Gln Leu Lys Val Leu Asp Cys Ala Met Asp Ala Cys Ile Asn Leu Gly
            330                 335                 340 ctg ttg gag gaa gcc ttg ttc tat ggt act cgg acc atg gag cca tac   1169
Leu Leu Glu Glu Ala Leu Phe Tyr Gly Thr Arg Thr Met Glu Pro Tyr
            345                 350                 355 agg att ttt ttc cca gga agc cat ccc gtc aga ggg gtt caa gtg atg   1217
Arg Ile Phe Phe Pro Gly Ser His Pro Val Arg Gly Val Gln Val Met
        360                 365                 370 aaa gtt ggc aaa ctg cag cta cat caa ggc atg ttt ccc caa gca atg   1265
Lys Val Gly Lys Leu Gln Leu His Gln Gly Met Phe Pro Gln Ala Met
375                 380                 385                 390
```

```
aag aat ctg aga ctg gct ttt gat att atg aga gtg aca cat ggc aga    1313
Lys Asn Leu Arg Leu Ala Phe Asp Ile Met Arg Val Thr His Gly Arg
            395                 400                 405 gaa cac agc ctg att gaa gat ttg att cta ctt tta gaa gaa tgc gac    1361
Glu His Ser Leu Ile Glu Asp Leu Ile Leu Leu Leu Glu Glu Cys Asp
        410                 415                 420 gcc aac atc aga gca tcc taa gggaacgcag tcagagggaa atacggcgtg       1412
Ala Asn Ile Arg Ala Ser
            425 tgtctttgtt gaatgcctta ttgaggtcac acactctatg ctttgttagc tgtgtgaacc  1472 tctcctattg gaaattctgt tccgtgtttg tgtaggtaaa taaaggcaga catggtttgc  1532 aaaccacaag aatcattagt tgtagagaag cacgattata ataaattcaa acatttggt   1592 tgaggatgcc aaaaaaaaaa aaaaaaaaa                                    1622

<210> SEQ ID NO 2
<211> LENGTH: 428
<212> TYPE: PRT
<213> ORGANISM: Homo sapiens

<400> SEQUENCE: 2

Met Glu Pro Leu Lys Val Glu Lys Phe Ala Thr Ala Asn Arg Gly Asn
1               5                   10                  15

Gly Leu Arg Ala Val Thr Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
    50                  55                  60

Cys Arg Val Ala Lys Tyr Cys Ser Ala Lys Cys Gln Lys Lys Ala Trp
65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125

Leu Glu Ser Asn Ile Asn Lys Leu Thr Glu Asp Lys Lys Glu Gly Leu
    130                 135                 140

Arg Gln Leu Val Met Thr Phe Gln His Phe Met Arg Glu Glu Ile Gln
145                 150                 155                 160

Asp Ala Ser Gln Leu Pro Pro Ala Phe Asp Leu Phe Glu Ala Phe Ala
                165                 170                 175

Lys Val Ile Cys Asn Ser Phe Thr Ile Cys Asn Ala Glu Met Gln Glu
            180                 185                 190

Val Gly Val Gly Leu Tyr Pro Ser Ile Ser Leu Leu Asn His Ser Cys
        195                 200                 205

Asp Pro Asn Cys Ser Ile Val Phe Asn Gly Pro His Leu Leu Leu Arg
    210                 215                 220

Ala Val Arg Asp Ile Glu Val Gly Glu Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Phe Arg Cys Gln Thr Gln Asp Lys Asp
            260                 265                 270
```

```
Ala Asp Met Leu Thr Gly Asp Glu Gln Val Trp Lys Glu Val Gln Glu
            275                 280                 285

Ser Leu Lys Lys Ile Glu Glu Leu Lys Ala His Trp Lys Trp Glu Gln
        290                 295                 300

Val Leu Ala Met Cys Gln Ala Ile Ile Ser Ser Asn Ser Glu Arg Leu
305                 310                 315                 320

Pro Asp Ile Asn Ile Tyr Gln Leu Lys Val Leu Asp Cys Ala Met Asp
                325                 330                 335

Ala Cys Ile Asn Leu Gly Leu Leu Glu Glu Ala Leu Phe Tyr Gly Thr
            340                 345                 350

Arg Thr Met Glu Pro Tyr Arg Ile Phe Phe Pro Gly Ser His Pro Val
        355                 360                 365

Arg Gly Val Gln Val Met Lys Val Gly Lys Leu Gln Leu His Gln Gly
    370                 375                 380

Met Phe Pro Gln Ala Met Lys Asn Leu Arg Leu Ala Phe Asp Ile Met
385                 390                 395                 400

Arg Val Thr His Gly Arg Glu His Ser Leu Ile Glu Asp Leu Ile Leu
                405                 410                 415

Leu Leu Glu Glu Cys Asp Ala Asn Ile Arg Ala Ser
            420                 425

<210> SEQ ID NO 3
<211> LENGTH: 5777
<212> TYPE: DNA
<213> ORGANISM: Homo sapiens
<220> FEATURE:
<221> NAME/KEY: CDS
<222> LOCATION: (250)..(4266)

<400> SEQUENCE: 3
gcggacactc ctctcggctc ctccccggca gcggcggcgg ctcggagcgg gctccggggc        60
tcgggtgcag cggccagcgg gcctggcggc gaggattacc cggggaagtg gttgtctcct       120
ggctggagcc gcgagacggg cgctcagggc gcggggccgg cggcggcgaa cgagaggacg       180
gactctggcg gccgggtcgt tggcggggga agcgcgggca ccgggcgagc aggccgcgtc       240 gcgctcacc atg gtc agc tac tgg gac acc ggg gtc ctg ctg tgc gcg ctg       291
          Met Val Ser Tyr Trp Asp Thr Gly Val Leu Leu Cys Ala Leu
            1               5                  10 ctc agc tgt ctg ctt ctc aca gga tct agt tca ggt tca aaa tta aaa        339
Leu Ser Cys Leu Leu Leu Thr Gly Ser Ser Ser Gly Ser Lys Leu Lys
 15                  20                  25                  30 gat cct gaa ctg agt tta aaa ggc acc cag cac atc atg caa gca ggc        387
Asp Pro Glu Leu Ser Leu Lys Gly Thr Gln His Ile Met Gln Ala Gly
                 35                  40                  45 cag aca ctg cat ctc caa tgc agg ggg gaa gca gcc cat aaa tgg tct        435
Gln Thr Leu His Leu Gln Cys Arg Gly Glu Ala Ala His Lys Trp Ser
             50                  55                  60 ttg cct gaa atg gtg agt aag gaa agc gaa agg ctg agc ata act aaa        483
Leu Pro Glu Met Val Ser Lys Glu Ser Glu Arg Leu Ser Ile Thr Lys
         65                  70                  75 tct gcc tgt gga aga aat ggc aaa caa ttc tgc agt act tta acc ttg        531
Ser Ala Cys Gly Arg Asn Gly Lys Gln Phe Cys Ser Thr Leu Thr Leu
 80                  85                  90 aac aca gct caa gca aac cac act ggc ttc tac agc tgc aaa tat cta        579
Asn Thr Ala Gln Ala Asn His Thr Gly Phe Tyr Ser Cys Lys Tyr Leu
 95                 100                 105                 110 gct gta cct act tca aag aag aag gaa aca gaa tct gca atc tat ata        627
Ala Val Pro Thr Ser Lys Lys Lys Glu Thr Glu Ser Ala Ile Tyr Ile
                115                 120                 125
```

```
ttt att agt gat aca ggt aga cct ttc gta gag atg tac agt gaa atc    675
Phe Ile Ser Asp Thr Gly Arg Pro Phe Val Glu Met Tyr Ser Glu Ile
        130                 135                 140 ccc gaa att ata cac atg act gaa gga agg gag ctc gtc att ccc tgc    723
Pro Glu Ile Ile His Met Thr Glu Gly Arg Glu Leu Val Ile Pro Cys
145                 150                 155 cgg gtt acg tca cct aac atc act gtt act tta aaa aag ttt cca ctt    771
Arg Val Thr Ser Pro Asn Ile Thr Val Thr Leu Lys Lys Phe Pro Leu
        160                 165                 170 gac act ttg atc cct gat gga aaa cgc ata atc tgg gac agt aga aag    819
Asp Thr Leu Ile Pro Asp Gly Lys Arg Ile Ile Trp Asp Ser Arg Lys
175                 180                 185                 190 ggc ttc atc ata tca aat gca acg tac aaa gaa ata ggg ctt ctg acc    867
Gly Phe Ile Ile Ser Asn Ala Thr Tyr Lys Glu Ile Gly Leu Leu Thr
                195                 200                 205 tgt gaa gca aca gtc aat ggg cat ttg tat aag aca aac tat ctc aca    915
Cys Glu Ala Thr Val Asn Gly His Leu Tyr Lys Thr Asn Tyr Leu Thr
            210                 215                 220 cat cga caa acc aat aca atc ata gat gtc caa ata agc aca cca cgc    963
His Arg Gln Thr Asn Thr Ile Ile Asp Val Gln Ile Ser Thr Pro Arg
        225                 230                 235 cca gtc aaa tta ctt aga ggc cat act ctt gtc ctc aat tgt act gct   1011
Pro Val Lys Leu Leu Arg Gly His Thr Leu Val Leu Asn Cys Thr Ala
240                 245                 250 acc act ccc ttg aac acg aga gtt caa atg acc tgg agt tac cct gat   1059
Thr Thr Pro Leu Asn Thr Arg Val Gln Met Thr Trp Ser Tyr Pro Asp
255                 260                 265                 270 gaa aaa aat aag aga gct tcc gta agg cga cga att gac caa agc aat   1107
Glu Lys Asn Lys Arg Ala Ser Val Arg Arg Arg Ile Asp Gln Ser Asn
                275                 280                 285 tcc cat gcc aac ata ttc tac agt gtt ctt act att gac aaa atg cag   1155
Ser His Ala Asn Ile Phe Tyr Ser Val Leu Thr Ile Asp Lys Met Gln
            290                 295                 300 aac aaa gac aaa gga ctt tat act tgt cgt gta agg agt gga cca tca   1203
Asn Lys Asp Lys Gly Leu Tyr Thr Cys Arg Val Arg Ser Gly Pro Ser
        305                 310                 315 ttc aaa tct gtt aac acc tca gtg cat ata tat gat aaa gca ttc atc   1251
Phe Lys Ser Val Asn Thr Ser Val His Ile Tyr Asp Lys Ala Phe Ile
320                 325                 330 act gtg aaa cat cga aaa cag cag gtg ctt gaa acc gta gct ggc aag   1299
Thr Val Lys His Arg Lys Gln Gln Val Leu Glu Thr Val Ala Gly Lys
335                 340                 345                 350 cgg tct tac cgg ctc tct atg aaa gtg aag gca ttt ccc tcg ccg gaa   1347
Arg Ser Tyr Arg Leu Ser Met Lys Val Lys Ala Phe Pro Ser Pro Glu
                355                 360                 365 gtt gta tgg tta aaa gat ggg tta cct gcg act gag aaa tct gct cgc   1395
Val Val Trp Leu Lys Asp Gly Leu Pro Ala Thr Glu Lys Ser Ala Arg
            370                 375                 380 tat ttg act cgt ggc tac tcg tta att atc aag gac gta act gaa gag   1443
Tyr Leu Thr Arg Gly Tyr Ser Leu Ile Ile Lys Asp Val Thr Glu Glu
        385                 390                 395 gat gca ggg aat tat aca atc ttg ctg agc ata aaa cag tca aat gtg   1491
Asp Ala Gly Asn Tyr Thr Ile Leu Leu Ser Ile Lys Gln Ser Asn Val
400                 405                 410 ttt aaa aac ctc act gcc act cta att gtc aat gtg aaa ccc cag att   1539
Phe Lys Asn Leu Thr Ala Thr Leu Ile Val Asn Val Lys Pro Gln Ile
415                 420                 425                 430 tac gaa aag gcc gtg tca tcg ttt cca gac ccg gct ctc tac cca ctg   1587
Tyr Glu Lys Ala Val Ser Ser Phe Pro Asp Pro Ala Leu Tyr Pro Leu
                435                 440                 445
```

| | |
|---|---|
| ggc agc aga caa atc ctg act tgt acc gca tat ggt atc cct caa cct<br>Gly Ser Arg Gln Ile Leu Thr Cys Thr Ala Tyr Gly Ile Pro Gln Pro<br>450 455 460 | 1635 |
| aca atc aag tgg ttc tgg cac ccc tgt aac cat aat cat tcc gaa gca<br>Thr Ile Lys Trp Phe Trp His Pro Cys Asn His Asn His Ser Glu Ala<br>465 470 475 | 1683 |
| agg tgt gac ttt tgt tcc aat aat gaa gag tcc ttt atc ctg gat gct<br>Arg Cys Asp Phe Cys Ser Asn Asn Glu Glu Ser Phe Ile Leu Asp Ala<br>480 485 490 | 1731 |
| gac agc aac atg gga aac aga att gag agc atc act cag cgc atg gca<br>Asp Ser Asn Met Gly Asn Arg Ile Glu Ser Ile Thr Gln Arg Met Ala<br>495 500 505 510 | 1779 |
| ata ata gaa gga aag aat aag atg gct agc acc ttg gtt gtg gct gac<br>Ile Ile Glu Gly Lys Asn Lys Met Ala Ser Thr Leu Val Val Ala Asp<br>515 520 525 | 1827 |
| tct aga att tct gga atc tac att tgc ata gct tcc aat aaa gtt ggg<br>Ser Arg Ile Ser Gly Ile Tyr Ile Cys Ile Ala Ser Asn Lys Val Gly<br>530 535 540 | 1875 |
| act gtg gga aga aac ata agc ttt tat atc aca gat gtg cca aat ggg<br>Thr Val Gly Arg Asn Ile Ser Phe Tyr Ile Thr Asp Val Pro Asn Gly<br>545 550 555 | 1923 |
| ttt cat gtt aac ttg gaa aaa atg ccg acg gaa gga gag gac ctg aaa<br>Phe His Val Asn Leu Glu Lys Met Pro Thr Glu Gly Glu Asp Leu Lys<br>560 565 570 | 1971 |
| ctg tct tgc aca gtt aac aag ttc tta tac aga gac gtt act tgg att<br>Leu Ser Cys Thr Val Asn Lys Phe Leu Tyr Arg Asp Val Thr Trp Ile<br>575 580 585 590 | 2019 |
| tta ctg cgg aca gtt aat aac aga aca atg cac tac agt att agc aag<br>Leu Leu Arg Thr Val Asn Asn Arg Thr Met His Tyr Ser Ile Ser Lys<br>595 600 605 | 2067 |
| caa aaa atg gcc atc act aag gag cac tcc atc act ctt aat ctt acc<br>Gln Lys Met Ala Ile Thr Lys Glu His Ser Ile Thr Leu Asn Leu Thr<br>610 615 620 | 2115 |
| atc atg aat gtt tcc ctg caa gat tca ggc acc tat gcc tgc aga gcc<br>Ile Met Asn Val Ser Leu Gln Asp Ser Gly Thr Tyr Ala Cys Arg Ala<br>625 630 635 | 2163 |
| agg aat gta tac aca ggg gaa gaa atc ctc cag aag aaa gaa att aca<br>Arg Asn Val Tyr Thr Gly Glu Glu Ile Leu Gln Lys Lys Glu Ile Thr<br>640 645 650 | 2211 |
| atc aga gat cag gaa gca cca tac ctc ctg cga aac ctc agt gat cac<br>Ile Arg Asp Gln Glu Ala Pro Tyr Leu Leu Arg Asn Leu Ser Asp His<br>655 660 665 670 | 2259 |
| aca gtg gcc atc agc agt tcc acc act tta gac tgt cat gct aat ggt<br>Thr Val Ala Ile Ser Ser Ser Thr Thr Leu Asp Cys His Ala Asn Gly<br>675 680 685 | 2307 |
| gtc ccc gag cct cag atc act tgg ttt aaa aac aac cac aaa ata caa<br>Val Pro Glu Pro Gln Ile Thr Trp Phe Lys Asn Asn His Lys Ile Gln<br>690 695 700 | 2355 |
| caa gag cct gga att att tta gga cca gga agc agc acg ctg ttt att<br>Gln Glu Pro Gly Ile Ile Leu Gly Pro Gly Ser Ser Thr Leu Phe Ile<br>705 710 715 | 2403 |
| gaa aga gtc aca gaa gag gat gaa ggt gtc tat cac tgc aaa gcc acc<br>Glu Arg Val Thr Glu Glu Asp Glu Gly Val Tyr His Cys Lys Ala Thr<br>720 725 730 | 2451 |
| aac cag aag ggc tct gtg gaa agt tca gca tac ctc act gtt caa gga<br>Asn Gln Lys Gly Ser Val Glu Ser Ser Ala Tyr Leu Thr Val Gln Gly<br>735 740 745 750 | 2499 |
| acc tcg gac aag tct aat ctg gag ctg atc act cta aca tgc acc tgt<br>Thr Ser Asp Lys Ser Asn Leu Glu Leu Ile Thr Leu Thr Cys Thr Cys<br>755 760 765 | 2547 |

```
gtg gct gcg act ctc ttc tgg ctc cta tta acc ctc ctt atc cga aaa    2595
Val Ala Ala Thr Leu Phe Trp Leu Leu Leu Thr Leu Leu Ile Arg Lys
            770                 775                 780 atg aaa agg tct tct tct gaa ata aag act gac tac cta tca att ata    2643
Met Lys Arg Ser Ser Ser Glu Ile Lys Thr Asp Tyr Leu Ser Ile Ile
        785                 790                 795 atg gac cca gat gaa gtt cct ttg gat gag cag tgt gag cgg ctc cct    2691
Met Asp Pro Asp Glu Val Pro Leu Asp Glu Gln Cys Glu Arg Leu Pro
    800                 805                 810 tat gat gcc agc aag tgg gag ttt gcc cgg gag aga ctt aaa ctg ggc    2739
Tyr Asp Ala Ser Lys Trp Glu Phe Ala Arg Glu Arg Leu Lys Leu Gly
815                 820                 825                 830 aaa tca ctt gga aga ggg gct ttt gga aaa gtg gtt caa gca tca gca    2787
Lys Ser Leu Gly Arg Gly Ala Phe Gly Lys Val Val Gln Ala Ser Ala
                835                 840                 845 ttt ggc att aag aaa tca cct acg tgc cgg act gtg gct gtg aaa atg    2835
Phe Gly Ile Lys Lys Ser Pro Thr Cys Arg Thr Val Ala Val Lys Met
            850                 855                 860 ctg aaa gag ggg gcc acg gcc agc gag tac aaa gct ctg atg act gag    2883
Leu Lys Glu Gly Ala Thr Ala Ser Glu Tyr Lys Ala Leu Met Thr Glu
        865                 870                 875 cta aaa atc ttg acc cac att ggc cac cat ctg aac gtg gtt aac ctg    2931
Leu Lys Ile Leu Thr His Ile Gly His His Leu Asn Val Val Asn Leu
    880                 885                 890 ctg gga gcc tgc acc aag caa gga ggg cct ctg atg gtg att gtt gaa    2979
Leu Gly Ala Cys Thr Lys Gln Gly Gly Pro Leu Met Val Ile Val Glu
895                 900                 905                 910 tac tgc aaa tat gga aat ctc tcc aac tac ctc aag agc aaa cgt gac    3027
Tyr Cys Lys Tyr Gly Asn Leu Ser Asn Tyr Leu Lys Ser Lys Arg Asp
                915                 920                 925 tta ttt ttt ctc aac aag gat gca gca cta cac atg gag cct aag aaa    3075
Leu Phe Phe Leu Asn Lys Asp Ala Ala Leu His Met Glu Pro Lys Lys
            930                 935                 940 gaa aaa atg gag cca ggc ctg gaa caa ggc aag aaa cca aga cta gat    3123
Glu Lys Met Glu Pro Gly Leu Glu Gln Gly Lys Lys Pro Arg Leu Asp
        945                 950                 955 agc gtc acc agc agc gaa agc ttt gcg agc tcc ggc ttt cag gaa gat    3171
Ser Val Thr Ser Ser Glu Ser Phe Ala Ser Ser Gly Phe Gln Glu Asp
    960                 965                 970 aaa agt ctg agt gat gtt gag gaa gag gag gat tct gac ggt ttc tac    3219
Lys Ser Leu Ser Asp Val Glu Glu Glu Glu Asp Ser Asp Gly Phe Tyr
975                 980                 985                 990 aag gag ccc atc act atg gaa gat ctg att  tct tac agt ttt caa    gtg 3267
Lys Glu Pro Ile Thr Met Glu Asp Leu Ile  Ser Tyr Ser Phe Gln    Val
                995                 1000                1005 gcc aga ggc atg  gag ttc ctg tct tcc  aga aag tgc att cat  cgg      3312
Ala Arg Gly Met  Glu Phe Leu Ser Ser  Arg Lys Cys Ile His  Arg
            1010                1015                1020 gac ctg gca gcg  aga aac att ctt tta  tct gag aac aac gtg  gtg      3357
Asp Leu Ala Ala  Arg Asn Ile Leu Leu  Ser Glu Asn Asn Val  Val
        1025                1030                1035 aag att tgt gat  ttt ggc ctt gcc cgg  gat att tat aag aac  ccc      3402
Lys Ile Cys Asp  Phe Gly Leu Ala Arg  Asp Ile Tyr Lys Asn  Pro
    1040                1045                1050 gat tat gtg aga  aaa gga gat act cga  ctt cct ctg aaa tgg  atg      3447
Asp Tyr Val Arg  Lys Gly Asp Thr Arg  Leu Pro Leu Lys Trp  Met
1055                1060                1065 gct ccc gaa tct  atc ttt gac aaa atc  tac agc acc aag agc  gac      3492
Ala Pro Glu Ser  Ile Phe Asp Lys Ile  Tyr Ser Thr Lys Ser  Asp
            1070                1075                1080
```

-continued

```
gtg tgg tct tac gga gta ttg ctg tgg gaa atc ttc tcc tta ggt      3537
Val Trp Ser Tyr Gly Val Leu Leu Trp Glu Ile Phe Ser Leu Gly
        1085                1090                1095 ggg tct cca tac cca gga gta caa atg gat gag gac ttt tgc agt      3582
Gly Ser Pro Tyr Pro Gly Val Gln Met Asp Glu Asp Phe Cys Ser
    1100                1105                1110 cgc ctg agg gaa ggc atg agg atg aga gct cct gag tac tct act      3627
Arg Leu Arg Glu Gly Met Arg Met Arg Ala Pro Glu Tyr Ser Thr
            1115                1120                1125 cct gaa atc tat cag atc atg ctg gac tgc tgg cac aga gac cca      3672
Pro Glu Ile Tyr Gln Ile Met Leu Asp Cys Trp His Arg Asp Pro
        1130                1135                1140 aaa gaa agg cca aga ttt gca gaa ctt gtg gaa aaa cta ggt gat      3717
Lys Glu Arg Pro Arg Phe Ala Glu Leu Val Glu Lys Leu Gly Asp
    1145                1150                1155 ttg ctt caa gca aat gta caa cag gat ggt aaa gac tac atc cca      3762
Leu Leu Gln Ala Asn Val Gln Gln Asp Gly Lys Asp Tyr Ile Pro
            1160                1165                1170 atc aat gcc ata ctg aca gga aat agt ggg ttt aca tac tca act      3807
Ile Asn Ala Ile Leu Thr Gly Asn Ser Gly Phe Thr Tyr Ser Thr
        1175                1180                1185 cct gcc ttc tct gag gac ttc ttc aag gaa agt att tca gct ccg      3852
Pro Ala Phe Ser Glu Asp Phe Phe Lys Glu Ser Ile Ser Ala Pro
    1190                1195                1200 aag ttt aat tca gga agc tct gat gat gtc aga tat gta aat gct      3897
Lys Phe Asn Ser Gly Ser Ser Asp Asp Val Arg Tyr Val Asn Ala
            1205                1210                1215 ttc aag ttc atg agc ctg gaa aga atc aaa acc ttt gaa gaa ctt      3942
Phe Lys Phe Met Ser Leu Glu Arg Ile Lys Thr Phe Glu Glu Leu
        1220                1225                1230 tta ccg aat gcc acc tcc atg ttt gat gac tac cag ggc gac agc      3987
Leu Pro Asn Ala Thr Ser Met Phe Asp Asp Tyr Gln Gly Asp Ser
    1235                1240                1245 agc act ctg ttg gcc tct ccc atg ctg aag cgc ttc acc tgg act      4032
Ser Thr Leu Leu Ala Ser Pro Met Leu Lys Arg Phe Thr Trp Thr
            1250                1255                1260 gac agc aaa ccc aag gcc tcg ctc aag att gac ttg aga gta acc      4077
Asp Ser Lys Pro Lys Ala Ser Leu Lys Ile Asp Leu Arg Val Thr
        1265                1270                1275 agt aaa agt aag gag tcg ggg ctg tct gat gtc agc agg ccc agt      4122
Ser Lys Ser Lys Glu Ser Gly Leu Ser Asp Val Ser Arg Pro Ser
    1280                1285                1290 ttc tgc cat tcc agc tgt ggg cac gtc agc gaa ggc aag cgc agg      4167
Phe Cys His Ser Ser Cys Gly His Val Ser Glu Gly Lys Arg Arg
            1295                1300                1305 ttc acc tac gac cac gct gag ctg gaa agg aaa atc gcg tgc tgc      4212
Phe Thr Tyr Asp His Ala Glu Leu Glu Arg Lys Ile Ala Cys Cys
        1310                1315                1320 tcc ccg ccc cca gac tac aac tcg gtg gtc ctg tac tcc acc cca      4257
Ser Pro Pro Pro Asp Tyr Asn Ser Val Val Leu Tyr Ser Thr Pro
    1325                1330                1335 ccc atc tag agtttgacac gaagccttat ttctagaagc acatgtgtat         4306
Pro Ile ttataccccc aggaaactag cttttgccag tattatgcat atataagttt acacctttat 4366 ctttccatgg gagccagctg cttttgtga ttttttaat agtgcttttt ttttttgact  4426
aacaagaatg taactccaga tagagaaata gtgacaagtg aagaacacta ctgctaaatc 4486 ctcatgttac tcagtgttag agaaatcctt cctaaaccca atgacttccc tgctccaacc 4546 cccgccacct cagggcacgc aggaccagtt tgattgagga gctgcactga tcacccaatg 4606
```

-continued

```
catcacgtac cccactgggc cagccctgca gcccaaaacc cagggcaaca agcccgttag    4666
ccccagggga tcactggctg gcctgagcaa catctcggga gtcctctagc aggcctaaga    4726
catgtgagga ggaaaaggaa aaaagcaaa aagcaaggga gaaagagaa accgggagaa      4786 ggcatgagaa agaatttgag acgcaccatg tgggcacgga gggggacggg gctcagcaat    4846
gccatttcag tggcttccca gctctgaccc ttctacattt gagggcccag ccaggagcag    4906
atggacagcg atgaggggac attttctgga ttctgggagg caagaaaagg acaaatatct    4966
tttttggaac taaagcaaat tttagacctt tacctatgga agtggttcta tgtccattct    5026
cattcgtggc atgttttgat ttgtagcact gagggtggca ctcaactctg agcccatact    5086
tttggctcct ctagtaagat gcactgaaaa cttagccaga gttaggttgt ctccaggcca    5146
tgatggcctt acactgaaaa tgtcacattc tattttgggt attaatatat agtccagaca    5206
cttaactcaa tttcttggta ttattctgtt ttgcacagtt agttgtgaaa gaaagctgag    5266
aagaatgaaa atgcagtcct gaggagagtt ttctccatat caaaacgagg gctgatggag    5326
gaaaaaggtc aataaggtca agggaagacc ccgtctctat accaaccaaa ccaattcacc    5386
aacacagttg ggacccaaaa cacaggaagt cagtcacgtt tccttttcat ttaatgggga    5446
ttccactatc tcacactaat ctgaaaggat gtggaagagc attagctggc gcatattaag    5506
cactttaagc tccttgagta aaaggtggt atgtaattta tgcaaggtat ttctccagtt     5566
gggactcagg atattagtta atgagccatc actagaagaa aagcccattt tcaactgctt    5626
tgaaacttgc ctggggtctg agcatgatgg gaatagggag acagggtagg aaagggcgcc    5686
tactcttcag ggtctaaaga tcaagtgggc cttggatcgc taagctggct ctgtttgatg    5746
ctatttatgc aagttagggt ctatgtattt a                                   5777
```

<210> SEQ ID NO 4
<211> LENGTH: 1338
<212> TYPE: PRT
<213> ORGANISM: Homo sapiens

<400> SEQUENCE: 4

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175
```

```
Leu Ile Pro Asp Gly Lys Arg Ile Ile Trp Asp Ser Arg Lys Gly Phe
        180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
    275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
        450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
        530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605
```

-continued

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
            645                 650                 655

Asp Gln Glu Ala Pro Tyr Leu Leu Arg Asn Leu Ser Asp His Thr Val
        660                 665                 670

Ala Ile Ser Ser Ser Thr Thr Leu Asp Cys His Ala Asn Gly Val Pro
    675                 680                 685

Glu Pro Gln Ile Thr Trp Phe Lys Asn Asn His Lys Ile Gln Gln Glu
690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
            725                 730                 735

Lys Gly Ser Val Glu Ser Ser Ala Tyr Leu Thr Val Gln Gly Thr Ser
        740                 745                 750

Asp Lys Ser Asn Leu Glu Leu Ile Thr Leu Thr Cys Thr Cys Val Ala
    755                 760                 765

Ala Thr Leu Phe Trp Leu Leu Leu Thr Leu Leu Ile Arg Lys Met Lys
770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
            805                 810                 815

Ala Ser Lys Trp Glu Phe Ala Arg Glu Arg Leu Lys Leu Gly Lys Ser
        820                 825                 830

Leu Gly Arg Gly Ala Phe Gly Lys Val Val Gln Ala Ser Ala Phe Gly
    835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
            885                 890                 895

Ala Cys Thr Lys Gln Gly Gly Pro Leu Met Val Ile Val Glu Tyr Cys
        900                 905                 910

Lys Tyr Gly Asn Leu Ser Asn Tyr Leu Lys Ser Lys Arg Asp Leu Phe
    915                 920                 925

Phe Leu Asn Lys Asp Ala Ala Leu His Met Glu Pro Lys Lys Glu Lys
930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
            965                 970                 975

Leu Ser Asp Val Glu Glu Glu Glu Asp Ser Asp Gly Phe Tyr Lys Glu
        980                 985                 990

Pro Ile Thr Met Glu Asp Leu Ile Ser Tyr Ser Phe Gln Val Ala Arg
    995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

```
Cys Asp Phe Gly Leu Ala Arg Asp Ile Tyr Lys Asn Pro Asp Tyr
1040                1045                1050

Val Arg Lys Gly Asp Thr Arg Leu Pro Leu Lys Trp Met Ala Pro
1055                1060                1065

Glu Ser Ile Phe Asp Lys Ile Tyr Ser Thr Lys Ser Asp Val Trp
1070                1075                1080

Ser Tyr Gly Val Leu Leu Trp Glu Ile Phe Ser Leu Gly Gly Ser
1085                1090                1095

Pro Tyr Pro Gly Val Gln Met Asp Glu Asp Phe Cys Ser Arg Leu
1100                1105                1110

Arg Glu Gly Met Arg Met Arg Ala Pro Glu Tyr Ser Thr Pro Glu
1115                1120                1125

Ile Tyr Gln Ile Met Leu Asp Cys Trp His Arg Asp Pro Lys Glu
1130                1135                1140

Arg Pro Arg Phe Ala Glu Leu Val Glu Lys Leu Gly Asp Leu Leu
1145                1150                1155

Gln Ala Asn Val Gln Gln Asp Gly Lys Asp Tyr Ile Pro Ile Asn
1160                1165                1170

Ala Ile Leu Thr Gly Asn Ser Gly Phe Thr Tyr Ser Thr Pro Ala
1175                1180                1185

Phe Ser Glu Asp Phe Phe Lys Glu Ser Ile Ser Ala Pro Lys Phe
1190                1195                1200

Asn Ser Gly Ser Ser Asp Asp Val Arg Tyr Val Asn Ala Phe Lys
1205                1210                1215

Phe Met Ser Leu Glu Arg Ile Lys Thr Phe Glu Glu Leu Leu Pro
1220                1225                1230

Asn Ala Thr Ser Met Phe Asp Asp Tyr Gln Gly Asp Ser Ser Thr
1235                1240                1245

Leu Leu Ala Ser Pro Met Leu Lys Arg Phe Thr Trp Thr Asp Ser
1250                1255                1260

Lys Pro Lys Ala Ser Leu Lys Ile Asp Leu Arg Val Thr Ser Lys
1265                1270                1275

Ser Lys Glu Ser Gly Leu Ser Asp Val Ser Arg Pro Ser Phe Cys
1280                1285                1290

His Ser Ser Cys Gly His Val Ser Glu Gly Lys Arg Arg Phe Thr
1295                1300                1305

Tyr Asp His Ala Glu Leu Glu Arg Lys Ile Ala Cys Cys Ser Pro
1310                1315                1320

Pro Pro Asp Tyr Asn Ser Val Val Leu Tyr Ser Thr Pro Pro Ile
1325                1330                1335
```

<210> SEQ ID NO 5
<211> LENGTH: 33
<212> TYPE: DNA
<213> ORGANISM: Artificial
<220> FEATURE:
<223> OTHER INFORMATION: PCR primer

<400> SEQUENCE: 5
cggaattccc cagatgaagt tcctttggat gag                          33

<210> SEQ ID NO 6
<211> LENGTH: 36
<212> TYPE: DNA
<213> ORGANISM: Artificial
<220> FEATURE:
<223> OTHER INFORMATION: PCR primer

<400> SEQUENCE: 6
ccgctcgaga atcagatctt ccatagtgat gggctc                          36

<210> SEQ ID NO 7
<211> LENGTH: 35
<212> TYPE: DNA
<213> ORGANISM: Artificial
<220> FEATURE:
<223> OTHER INFORMATION: PCR primer

<400> SEQUENCE: 7
cggaattcga tttcttacag ttttcaagtg gccag                           35

<210> SEQ ID NO 8
<211> LENGTH: 36
<212> TYPE: DNA
<213> ORGANISM: Artificial
<220> FEATURE:
<223> OTHER INFORMATION: PCR primer

<400> SEQUENCE: 8
ccgctcgaga gctgaaatac tttccttgaa gaagtc                          36

<210> SEQ ID NO 9
<211> LENGTH: 36
<212> TYPE: DNA
<213> ORGANISM: Artificial
<220> FEATURE:
<223> OTHER INFORMATION: PCR primer

<400> SEQUENCE: 9
cggaattcag ctccgaagtt taattcagga agctct                          36

<210> SEQ ID NO 10
<211> LENGTH: 34
<212> TYPE: DNA
<213> ORGANISM: Artificial
<220> FEATURE:
<223> OTHER INFORMATION: PCR primer

<400> SEQUENCE: 10
ccgctcgagc tagatgggtg gggtggagta cagg                            34

<210> SEQ ID NO 11
<211> LENGTH: 36
<212> TYPE: DNA
<213> ORGANISM: Artificial
<220> FEATURE:
<223> OTHER INFORMATION: PCR primer

<400> SEQUENCE: 11
ccgctcgagc acttttccaa aagcccctct tccaag                          36

<210> SEQ ID NO 12
<211> LENGTH: 36
<212> TYPE: DNA
<213> ORGANISM: Artificial
<220> FEATURE:
<223> OTHER INFORMATION: PCR primer

<400> SEQUENCE: 12
cggaattcgg ttcaagcatc agcatttggc attaag                          36

<210> SEQ ID NO 13
<211> LENGTH: 35
<212> TYPE: DNA
<213> ORGANISM: Artificial
<220> FEATURE:
<223> OTHER INFORMATION: PCR primer

<400> SEQUENCE: 13
ccgctcgagc tcagtcatca gagctttgta ctcgc         35

<210> SEQ ID NO 14
<211> LENGTH: 36
<212> TYPE: DNA
<213> ORGANISM: Artificial
<220> FEATURE:
<223> OTHER INFORMATION: PCR primer

<400> SEQUENCE: 14
cggaattcgc taaaaatctt gacccacatt ggccac        36

<210> SEQ ID NO 15
<211> LENGTH: 37
<212> TYPE: DNA
<213> ORGANISM: Artificial
<220> FEATURE:
<223> OTHER INFORMATION: PCR primer

<400> SEQUENCE: 15
ccgctcgagg tagttggaga gatttccata tttgcag       37

<210> SEQ ID NO 16
<211> LENGTH: 31
<212> TYPE: DNA
<213> ORGANISM: Artificial
<220> FEATURE:
<223> OTHER INFORMATION: PCR primer

<400> SEQUENCE: 16
ccgctcgagc ttggtgcagg ctcccagcag g              31

<210> SEQ ID NO 17
<211> LENGTH: 39
<212> TYPE: DNA
<213> ORGANISM: Artificial
<220> FEATURE:
<223> OTHER INFORMATION: PCR primer

<400> SEQUENCE: 17
ctcccttatg atgccagcgc gtgggagttt gcccgggag      39

<210> SEQ ID NO 18
<211> LENGTH: 39
<212> TYPE: DNA
<213> ORGANISM: Artificial
<220> FEATURE:
<223> OTHER INFORMATION: PCR primer

<400> SEQUENCE: 18
ctcccgggca aactcccacg cgctggcatc ataagggag      39

<210> SEQ ID NO 19
<211> LENGTH: 40
<212> TYPE: DNA
<213> ORGANISM: Artificial
<220> FEATURE:
<223> OTHER INFORMATION: PCR primer

<400> SEQUENCE: 19
gacttaaact gggcgcatca cttggaagag gggcttttgg                    40

<210> SEQ ID NO 20
<211> LENGTH: 40
<212> TYPE: DNA
<213> ORGANISM: Artificial
<220> FEATURE:
<223> OTHER INFORMATION: PCR primer

<400> SEQUENCE: 20
ccaaaagccc ctcttccaag tgatgcgccc agtttaagtc                    40

<210> SEQ ID NO 21
<211> LENGTH: 39
<212> TYPE: DNA
<213> ORGANISM: Artificial
<220> FEATURE:
<223> OTHER INFORMATION: PCR primer

<400> SEQUENCE: 21
ctcccttatg atgccagcga gtgggagttt gcccgggag                     39

<210> SEQ ID NO 22
<211> LENGTH: 39
<212> TYPE: DNA
<213> ORGANISM: Artificial
<220> FEATURE:
<223> OTHER INFORMATION: PCR primer

<400> SEQUENCE: 22
ctcccgggca aactcccact cgctggcatc ataagggag                     39

<210> SEQ ID NO 23
<211> LENGTH: 40
<212> TYPE: DNA
<213> ORGANISM: Artificial
<220> FEATURE:
<223> OTHER INFORMATION: PCR primer

<400> SEQUENCE: 23
gacttaaact gggcgaatca cttggaagag gggcttttgg                    40

<210> SEQ ID NO 24
<211> LENGTH: 40
<212> TYPE: DNA
<213> ORGANISM: Artificial
<220> FEATURE:
<223> OTHER INFORMATION: PCR primer

<400> SEQUENCE: 24
ccaaaagccc ctcttccaag tgattcgccc agtttaagtc                    40

<210> SEQ ID NO 25
<211> LENGTH: 39
<212> TYPE: DNA
<213> ORGANISM: Artificial
<220> FEATURE:
<223> OTHER INFORMATION: PCR primer

<400> SEQUENCE: 25
ctcccttatg atgccagccg gtgggagttt gcccgggag                     39

```
<210> SEQ ID NO 26
<211> LENGTH: 39
<212> TYPE: DNA
<213> ORGANISM: Artificial
<220> FEATURE:
<223> OTHER INFORMATION: PCR primer

<400> SEQUENCE: 26
ctcccgggca aactcccacc ggctggcatc ataagggag                              39

<210> SEQ ID NO 27
<211> LENGTH: 40
<212> TYPE: DNA
<213> ORGANISM: Artificial
<220> FEATURE:
<223> OTHER INFORMATION: PCR primer

<400> SEQUENCE: 27
gacttaaact gggccgatca cttggaagag gggcttttgg                             40

<210> SEQ ID NO 28
<211> LENGTH: 40
<212> TYPE: DNA
<213> ORGANISM: Artificial
<220> FEATURE:
<223> OTHER INFORMATION: PCR primer

<400> SEQUENCE: 28
ccaaaagccc ctcttccaag tgatcggccc agtttaagtc                             40

<210> SEQ ID NO 29
<211> LENGTH: 34
<212> TYPE: DNA
<213> ORGANISM: Artificial
<220> FEATURE:
<223> OTHER INFORMATION: PCR primer

<400> SEQUENCE: 29
cggaattcac ccagatgaag ttcctttgga tgag                                   34

<210> SEQ ID NO 30
<211> LENGTH: 39
<212> TYPE: DNA
<213> ORGANISM: Artificial
<220> FEATURE:
<223> OTHER INFORMATION: PCR primer

<400> SEQUENCE: 30
aagcttgcgg ccgcgatgga gccgctgaag gtggaaaag                              39

<210> SEQ ID NO 31
<211> LENGTH: 36
<212> TYPE: DNA
<213> ORGANISM: Artificial
<220> FEATURE:
<223> OTHER INFORMATION: PCR primer

<400> SEQUENCE: 31
ggtacctcta gattaggatg ctctgatgtt ggcgtc                                 36

<210> SEQ ID NO 32
<211> LENGTH: 38
<212> TYPE: DNA
<213> ORGANISM: Artificial
<220> FEATURE:
<223> OTHER INFORMATION: PCR primer
```

<400> SEQUENCE: 32
ggggtacctc aaatcagatc ttccatagtg atgggctc                        38

<210> SEQ ID NO 33
<211> LENGTH: 38
<212> TYPE: DNA
<213> ORGANISM: Artificial
<220> FEATURE:
<223> OTHER INFORMATION: PCR primer

<400> SEQUENCE: 33
ggggtacctc aagctgaaat actttccttg aagaagtc                        38

<210> SEQ ID NO 34
<211> LENGTH: 33
<212> TYPE: DNA
<213> ORGANISM: Artificial
<220> FEATURE:
<223> OTHER INFORMATION: PCR primer

<400> SEQUENCE: 34
ggggtaccct agatgggtgg ggtggagtac agg                             33

<210> SEQ ID NO 35
<211> LENGTH: 35
<212> TYPE: DNA
<213> ORGANISM: Artificial
<220> FEATURE:
<223> OTHER INFORMATION: PCR primer

<400> SEQUENCE: 35
cggaattccg ccgtgacccc gctggcgccc cggag                           35

<210> SEQ ID NO 36
<211> LENGTH: 32
<212> TYPE: DNA
<213> ORGANISM: Artificial
<220> FEATURE:
<223> OTHER INFORMATION: PCR primer

<400> SEQUENCE: 36
ggggtacctt aggatgctct gatgttggcg tc                              32

<210> SEQ ID NO 37
<211> LENGTH: 32
<212> TYPE: DNA
<213> ORGANISM: Artificial
<220> FEATURE:
<223> OTHER INFORMATION: PCR primer

<400> SEQUENCE: 37
cggaattctg actccgttcg acttcttggc ag                              32

<210> SEQ ID NO 38
<211> LENGTH: 36
<212> TYPE: DNA
<213> ORGANISM: Artificial
<220> FEATURE:
<223> OTHER INFORMATION: PCR primer

<400> SEQUENCE: 38
cggaattctc ggaagcagct gagggaccag tactgc                          36

```
<210> SEQ ID NO 39
<211> LENGTH: 33
<212> TYPE: DNA
<213> ORGANISM: Artificial
<220> FEATURE:
<223> OTHER INFORMATION: PCR primer

<400> SEQUENCE: 39
ggggtacctt agttaccggc gctcctcctg gtc                                    33
```

METHODS OF IDENTIFYING AGENTS THAT MODULATE METHYLATION OF VEGFR1 BY SMYD3

CROSS REFERENCES TO RELATED APPLICATIONS

This application is a U.S. National Stage Application of PCT/JP2008/001516, filed Jun. 13, 2008, which claims the benefit of U.S. Provisional Application Ser. No. 60/944,071, filed Jun. 14, 2007, the contents of which are hereby incorporated by reference in their entirety.

TECHNICAL FIELD

The present invention relates to transcriptional regulation, more particularly to the identification of agents that modulate methyltransferase activity, such as agents that modulate methylation of VEGFR1 by SMYD3 (also known as "ZNFN3A1"). As SMYD3 is up-regulated in a number of cancer types, SMYD3 modulators so identified may prove useful in the treatment of cancer, including, for example, colorectal carcinoma, hepatocellular carcinoma, bladder cancer and breast cancer.

BACKGROUND ART

Modifications of histone tails play a crucial role for the regulation of transcription, telomere maintenance, DNA replication, and chromosome segregation (Kouzarides T, Cell 2007, 128(4): 693-705). Examples of such modifications include acetylation, phosphorylation, methylation, and/or ubiquitination. Covalent modifications in particular regulate not only the chromatin structure but also the interaction with chromatin binding proteins (Kouzarides T, Cell 2007, 128(4): 693-705; Strahl B D and Allis C D, Nature 2000, 403(6765): 41-5; Jenuwein T and Allis C D, Science 2001, 293(5532): 1074-80). In addition, methylation of H3K4, H3K36, and H3K79 is associated with euchromatin structure, whereas that of H3K9, H3K27, and H4K20 is associated with heterochromatin structure (Strahl B D and Allis C D, Nature 2000, 403(6765): 41-5; Jenuwein T and Allis C D, Science 2001, 293(5532): 1074-80).

Conformation of chromatin is one of the key regulators of transcription; untranscribed genes are compacted in heterochromatin, while transcribed genes are in euchromatin, where transcriptional complexes are accessible to the target DNA (Li B et al., Cell 2007, 128(4): 707-19). In addition, modification of histone residue facilitates the interaction with its binding protein(s), and affects subsequent modifications on other histone tails (Strahl B D and Allis C D, Nature 2000, 403(6765): 41-5; Jenuwein T and Allis C D, Science 2001, 293(5532): 1074-80; Li B et al., Cell 2007, 128(4): 707-19; Zhang Y and Reinberg D, Genes & development 2001, 15(18): 2343-60). For example, phosphorylation of H3 serine 10 (H3S10) suppresses methylation of H3K9. Conversely, methylation of H3K9 antagonizes phosphorylation of H3S10. Phosphorylation of H3S10 promotes acetylation of H3K14 by GCN5 (Zhang Y and Reinberg D, Genes & development 2001, 15(18): 2343-60).

The methylation of H3K9 is involved in the transport of HP1 to distinct chromosomal areas, which, in turn, is crucial for establishing and maintaining domains of heterochromatin (Nakayama J et al., Science 2001, 292(5514): 110-3; Lachner M et al., Nature 2001, 410(6824): 116-20; Bannister A J et al., Nature 2001, 410(6824): 120-4). Recruitment of HP1 proteins to certain sites of the genome involves interactions with multiple components of chromatin (Nielsen S J et al., Nature 2001, 412(6846): 561-5). This recruitment is believed to suppress methylation of H3K4, a protein that is crucial for transcriptional activation. These data indicate the complex nature of histone modification that is regulated by the interplay between different modifications. Indeed, a growing number of these proteins have been shown to promote or inhibit tumourigenesis through their histone methyltransferase activity (Varambally S et al., Nature 2002, 419(6907): 624-9; Hamamoto R et al., S Nature cell biology 2004, 6(8): 731-40; Gibbons R J, Human molecular genetics 2005, 14 Spec No 1: R85-92).

Although methylation of histone tails has been intensively studied, that of non-histone protein remains unclear. Recent studies reported that SET7/9, a histone H3K4 MTase, catalyzes TAF10 and p53 as substrates (Kouskouti A et al., Mol Cell 2004, 14(2): 175-82; Chuikov S et al., Nature 2004, 432(7015): 353-60.) Vascular endothelial growth factor receptor-1 (VEGFR1) (Accession No.: NM_002019) is a receptor tyrosine kinase (RTK) that plays a role in physiological and pathological angiogenesis in the context of receptor dimerization and an interaction with its ligands (Shibuya M et al., Oncogene 1990, 5(4): 519-24; Rahimi N, Experimental eye research 2006, 83(5): 1005-16).

VEGFR1 shares structural similarity with the FMS/KIT/PDGFR family, containing an extracellular domain, seven immunoglobulin (Ig)-like sequences, and a cytoplasmic tyrosine kinase domain with a long kinase insert. VEGFR1 is expressed in two forms, as a full-length tyrosine kinase receptor and in a soluble form that carries only the extracellular domain. Through homodimerization or heterodimerization with other RTKs such as VEGFR2 and VEGFR3, the full-length form of VEGFR1 positively mediates signaling on binding with its ligands. However, the soluble form of VEGFR1 acts as an inhibitor through ligand trapping, and suppresses angiogenesis (Shibuya M, Journal of biochemistry and molecular biology 2006, 39(5): 469-78). The regulatory mechanism of these opposite functions remains unclear.

Although one VEGFR ligand, vascular endothelial growth factor-A (VEGFA), associates with both VEGFR1 and VEGFR2, the affinity of VEGFA to VEGFR1 is at least one order of magnitude higher than that to VEGFR2 (Sawano A et al., Cell Growth Differ 1996, 7(2): 213-21). On the other hand, the endogenous tyrosine kinase activity of VEGFR1 is extremely low as compared with that of VEGFR2. Upon binding with VEGFA, these receptors dramatically increase their autophosphorylation levels, and induce growth of endothelial cells (ECs), recruitment of EC progenitors, adhesion of natural killer cells to ECs and monocyte migration (Shibuya M et al., Oncogene 1990, 5(4): 519-24; Rahimi N, Experimental eye research 2006, 83(5): 1005-16; Shibuya M, Journal of biochemistry and molecular biology 2006, 39(5): 469-78). Although several VEGFR1 tyrosine-phosphorylation sites and their potential interacting partners have been described in different expression models (Shibuya M, Journal of biochemistry and molecular biology 2006, 39(5): 469-78), the downstream signaling events remain to be delineated, primarily due to the low biological activity of this receptor.

The present inventors previously reported that SMYD3 (Accession No.: AB057595) has di- and tri-methyltransferase activity on lysine 4 of histone H3 (H3-K4) (See WO 2005/071102, the entire contents of which are incorporated by reference herein). In addition, previous reports demonstrate that elevated SMYD3 expression plays a crucial role in the proliferation of colorectal carcinoma (CRC) and hepatocellular carcinoma (HCC) cells (See WO 2003/027143, the entire contents of which are incorporated by reference herein;

see also Hamamoto, R. et al., Nat Cell Biol 6, 731-40 (2004)) and Hamamoto R et al., Cancer Sci 2006, 97(2): 113-8). In particular, over-expression of SMYD3 was shown to result in growth promotion of NIH3T3 cells while the knockdown of endogenous SMYD3 expression in several cancer cells was shown to induce growth inhibition and apoptosis of those cells. The present inventors also have shown that retinoblastoma protein (R1) is methylated through interaction with the SET domain of SMYD3, and that such methylation facilitates phosphorylations of RB1 at threonines 821/826 and serines 807/811 by CDK2/cyclinE or CDK6/cyclinD3 complex in vitro and in vivo (See WO2007/004526, the entire contents of which are incorporated by reference herein).

Patent Citation 1: WO2003/027143 (JP 2005-511023)
Patent Citation 2: WO2004/076623 (JP 2006-519009)
Patent Citation 3: WO2005/071102 (JP 2007-519391)
Patent Citation 4: WO 2006/092958, A1
Patent Citation 5: WO 2007/004526, A2
Non Patent Citation 1: Kunizaki, et al. Cancer Res. 2007 Nov. 15; 67(22):10759-65

SUMMARY OF THE INVENTION

In searching for other substrates of SMYD3 methyltransferase, the present inventors found that SMYD3 methylates lysine 831 of VEGFR1 in vitro and in vivo, and that such VEGFR1 methylation enhances its kinase activity. These findings will lead to a better understanding of the regulatory mechanisms of VEGFR1 and human carcinogenesis.

Accordingly, the present invention is based, at least in part, on the discovery of a novel mechanism of VEGFR1 regulation, through lysine 831 methylation by SMYD3. SMYD3, also known under the gene name "ZNFN3A1", is a histone H3 methyltransferase that is up-regulated in a great majority of colorectal and hepatocellular carcinomas (See, for example, WO 2003/027143 cited above) as well as bladder and breast cancers (See, for example, WO 2006/085684 and WO 2006/092958) each of which in incorporated by reference herein in its entirety.

As demonstrated herein, VEGFR1 interacts with the SET domain of SMYD3. This interaction results in the methylation of VEGFR1, which, as shown herein, results in enhanced kinase activity in vitro. These findings provide for a more profound understanding of the biological role of SMYD3 as well as the regulatory mechanisms of VEGFR1. In addition, the present findings contribute to the better understanding of carcinogenesis, more particularly colorectal, hepatocellular, bladder and breast carcinogenesis, and thus contribute to the development new therapeutic strategies for these tumors.

Accordingly, it is an object of the present invention to provide a method for identifying an agent that modulates methylation of VEGFR1 by SMYD3, the method including the steps of:

(a) contacting an SMYD3 polypeptide having a methyltransferase activity with a VEGFR1 peptide to be methylated and a cofactor in the presence of a test agent under conditions suitable for the methylation of the VEGFR1 peptide;

(b) detecting the methylation level of the VEGFR1 peptide; and (c) comparing the methylation level detected in step (b) with a control level detected in the absence of the agent.

wherein an increase or decrease in the methylation level as compared to the control level indicates that the agent modulates methylation of VEGFR1 by SMYD3.

It is a further object of the present invention to provide a kit for detecting for the ability of a test compound to regulate methylation of VEGFR1, such a kit including (a) an SMYD3 polypeptide having methyltransferase activity, (b) a VEGFR1 peptide capable of being methylated by the SMYD3 polypeptide, and (c) a cofactor for the methylation of the VEGFR1 peptide. In a further embodiment, the kit may optionally include S-adenosyl homocysteine hydrolase (SAHH).

The present invention further provides a method of screening for a compound for treating a cancer, such as colorectal cancer, hepatocellular carcinoma, bladder and breast cancer, such a method including the steps of: (a) identifying a test compound that modulates methylation according to the method described above, and (b) selecting the test compound that decreases the methylation level of the substrate to be methylated as compared to a control methylation level detected in the absence of the test compound.

The present invention further provides a method of measuring methyltransferase activity of a polypeptide, said method including the steps of:

a. contacting a polypeptide selected from the group consisting of:

i. a polypeptide having the amino acid sequence of SEQ ID NO: 2 (SMYD3);

ii. a polypeptide having the amino acid sequence of SEQ ID NO: 2 wherein one or more amino acids are substituted, deleted, or inserted, and said polypeptide has a biological activity equivalent to the polypeptide having the amino acid sequence of SEQ ID NO: 2;

iii. a polypeptide having an amino acid sequence that is at least about 80% homologous to SEQ ID NO: 2;

vi. a polypeptide encoded by a polynucleotide that hybridizes under stringent conditions to a polynucleotide having the nucleotide sequence of SEQ ID NO: 1, wherein the polypeptide has a biological activity equivalent to a polypeptide corresponding to the amino acid sequence of SEQ ID NO: 2; and v. a polypeptide that includes the amino acid sequence of positions 117 to 246 of the amino acid sequence of SEQ ID NO: 2, wherein said polypeptide has a methyltransferase activity equivalent to the polypeptide having the amino acid sequence of SEQ ID NO:2;

with a VEGFR1 peptide to be methylated and a cofactor under the condition capable of methylation of the VEGFR1 peptide;

b. detecting the methylation level of the VEGFR1 peptide; and c. measuring the methyltransferase activity by correlating the methylation level of step (b) with the methyltransferase activity.

Alternatively, the present invention also provides a kit for measuring the methyltransferase activity of SMYD3, said kit including the following components:

a. a VEGFR1 peptide capable of being methylated by the SMYD3, b. a cofactor for the methylation of the VEGFR1 peptide, and c. a detection regent for detecting methylated of lysine 831.

These and other objects, features and advantages of the invention will become more fully apparent when the following detailed description is read in conjunction with the accompanying figures and examples, as well as the claims appended hereto.

Unless otherwise defined, all technical and scientific terms used herein have the same meaning as commonly understood by one of ordinary skill in the art to which this invention belongs. In addition, the words "a", "an" and "the" as used herein mean "at least one" unless otherwise specifically indicated.

Although methods and materials similar or equivalent to those described herein can be used in the practice or testing of the present invention, examples of suitable methods and materials are described herein below.

All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

FIG. 1 depicts the methylation of the cytoplasmic region of VEGFR1 in vitro. Part a depicts the results of an in vitro MTase assay of SMYD3 using as a substrate recombinant proteins VEGFR1#1, #2, and #3, each of which contain different cytoplasmic regions of VEGFR1. Ig-LD corresponds to an immunoglobulin-like domain, TM to a transmembrane domain, TK to a tyrosine kinase domain. Recombinant VEGFR1#1, #2, and #3 proteins were incubated with $^3$H-labeled SAM, a methyl donor, in the presence (closed box) or absence of immunoprecipitated Flag-tagged SMYD3. Methylated substrates were quantified by liquid scintillation counter. Immunoprecipitants from cells transfected with mock plasmid were used for control (opened box). Independent experiments were carried out three times with different immunoprecipitants. Part b depicts the detection of methylated VEGFR1 by fluorogram. Recombinant SMYD3 was incubated with recombinant VEGFR1 in the presence or absence of S-(5'-Adenosyl)-L-homocysteine hydrolase (SAHH). The substrates were quantified by immunoblot analysis with anti-GST antibody (lower panel). Part c depicts the determination of the methylated region in VEGFR1#1.

FIG. 2 depicts the methylation of VEGFR1 lysine 831 both in vitro and in vivo. Part a depicts the alignment of flanking sequences of methylated lysines by histone methyltransferases and candidate lysines in VEGFR1 (asterisks). Part b depicts the in vitro methylation of wild type and mutant forms (K819A and K831A) of VEGFR1-N1 (upper panel). Part c depicts the in vitro methylation of VEGFR1 mutants containing different substitutions of VEGFR1-K831. Part d depicts the in vitro methylation of VEGFR1 was detected by immunoblot analysis with anti-methylated K831 (K831me2)-specific antibody (middle panel). Methylation was confirmed in a different experiment by fluorogram (upper panel). VEGFR1 was quantified by immunoblot analysis with anti-GST antibody (lower panel). Part e depicts the methylation of VEGFR1 in 293-SMYD3 cells expressing HA-tagged VEGFR1 and 293-Mock cells. The cells were treated with L-[methyl-$^3$H]methionine in the presence of protein synthesis inhibitor. VEGFR1 was immunoprecipitated with anti-HA antibody, and examined by fluorogram (upper panel). Part f depicts the methylation of VEGFR1 detected by immunoblot analysis with anti-methylated K831 (K831me2)-specific antibody. Part g depicts the suppression of K831 methylation by knockdown of SMYD3. Whole cell extracts from 293-SMYD3 cells, treated with SMYD3-specific siRNA or control siRNA, were used for immunoblot analysis.

FIG. 3 depicts the interaction between SMYD3 and VEGFR1. Part a depicts the interaction between SMYD3 and VEGFR1, examined by a co-immunoprecipitation assay using extract from HEK293 cells expressing HA-tagged SMYD3 and different regions of Flag-tagged VEGFR1 (VEGFR1#1, #2, and #3). Part b depicts the interaction of endogenous SMYD3 with VEGFR1. Whole cell extracts from SNU423, SW480, and MCF7 cells expressing both SMYD3 and VEGFR1 were precipitated with anti-SMYD3 antibody. The precipitants were immunoblotted with anti-VEGFR-1 antibody (upper panel) or anti-SMYD3 antibody (lower panel). Part c depicts the association of VEGFR1 with the SET domain of SMYD3. Wild type or deleted forms of Flag-tagged SMYD3 (N-20, delta 2, or delta 3) were co-expressed with HA-tagged VEGFR1 in HEK293 cells. IP was performed with either anti-HA or anti-Flag antibody, and the precipitants were analyzed by western blot analysis with anti-Flag (upper panel) or anti-HA (lower panel) antibody. Part d depicts the interaction of the cytoplasmic region of VEGFR1 with the SET domain of SMYD3 in vivo. Flag-tagged wild type or the SET domain of SMYD3 was co-expressed with HA-tagged VEGFR1 in HEK293 cells. Extracts from the cells were precipitated with anti-Flag (upper panel) or anti-HA (lower panel) antibodies, and the precipitants were analyzed by western blot analysis with anti-HA antibody.

The results shown in FIG. 4 demonstrate that the kinase activity of VEGFR1 is enhanced by its methylation. Part a depicts the results of an in vitro kinase assay carried out using methylated or unmethylated VEGFR1. Recombinant GST-fused VEGFR1 was treated with (closed box) or without (opened box) SMYD3. Its kinase activity was subsequently analyzed using its peptide substrates. Phosphorylated substrates were detected with anti-phospho-Tyrosine antibody and quantified by fluoroimmunoassay with specific secondary antibody. The results shown in Part b demonstrate that the autophosphorylation of recombinant VEGFR1 protein is enhanced by SMYD3. VEGFR1 was separated on PAGE-SDS and subsequently transferred to nitrocellulose membrane. Immunoblot analysis was carried out with anti-phosphotyrosine or anti-VEGFR1 antibody.

DETAILED DESCRIPTION OF THE INVENTION

The SMYD3 cDNA consists of 1622 nucleotides that contain an open reading frame of 1284 nucleotides as set forth in SEQ. ID. NO.: 1. The open reading frame encodes a 428-amino acid protein with a zinc finger motif and a SET domain, as shown in SEQ. ID. NO.: 2. The zinc finger domain (MYND) extends from amino acid 49 to amino acid 87 and the SET (Su 3-9, Enhancer-of-zeste, Trihorrax) domain extends from amino acid 117 to amino acid 246.

The subcellular localization of the SMYD3 protein is altered during cell cycle progression and by the density of cultured cells. The SMYD3 protein accumulates in the nucleus when cells are in middle to late S phase or cultured in sparse conditions. However, the SMYD3 protein localizes in the cytoplasm as well as in the nucleus when cells are in other phases of the cell cycle or grown in a dense condition.

The present invention provides a method for determining the methyltransferase activity of SMYD3 for methylating a VEGFR1 substrate. The method may be practiced by contacting an SMYD3 polypeptide, or a functional equivalent thereof having methyltransferase activity, with a VEGFR1 protein, and assaying the methyltransferase activity of the contacted SMYD3 or its functional equivalent. In this context, the methyltransferase activity of SMYD3 corresponds to the degree of VEGFR1 methylation. Accordingly, methyltransferase activity can be measured by detecting the methylation level of the VEGFR1 substrate. More particularly, in the context of the instant invention, the methyltransferase activity to be measured can be calibrated to methylation level of the VEGFR1 peptide through correlation with a reference sample. In the context of the present invention, any biological sample having known methyltransferase activity may be used as the reference sample. For example, the requisite calibration curve may be obtained through the serial dilution of purified SMYD3 peptide.

In addition, a method for screening for modulators of methyltransferase activity is also provided. The present invention thus provides a method of screening for an agent that modulates SMYD3 methyltransferase activity. The method may be practiced by contacting an SMYD3 polypeptide, or a functional equivalent thereof having methyltransferase activity, with a VEGFR1 protein, and assaying the methyltransferase activity of the contacted SMYD3 or its functional equivalent. An agent that modulates the methyltransferase activity of the SMYD3 or functional equivalent can be thereby identified.

In the context of the present invention, the term "functionally equivalent" means that the subject protein or polypeptide has the same or substantially the same methyltransferase activity as SMYD3. In particular, the protein catalyzes the methylation of a VEGFR1 protein or a fragment of a VEGFR1 protein that includes lysine 831. Whether a subject protein has the target activity can be routinely determined by the present invention. Namely, the methyltransferase activity can be determined by (a) contacting a polypeptide with a substrate (e.g., a VEGFR1 protein or a fragment that includes lysine 831) and a co-factor (e.g., S-adenosyl-L-methionine) under conditions suitable for methylation of the substrate, and (b) detecting the methylation level of the substrate.

As used herein, the term "VEGFR1 peptide" refers to full length VEGFR1 proteins (e.g., SEQ ID NO: 4) as well as functional mutants and fragments thereof. Examples of functional fragments include, but are not limited to, C-terminal fragment such as the fragment composed of amino acids 800 to 841 of SEQ ID NO: 4. Preferred fragments include the lysine residue at position 831. Examples of functional mutants include, but are not limited to, the following VEGFR1 mutants that retain the methylation capacity of the full length VEGFR1 protein: K819A, K819E and K819R.

Methods for preparing proteins that are functional equivalents of a given protein are well known to those skilled in the art and include conventional methods of introducing mutations into the protein. For example, one skilled in the art can prepare proteins functionally equivalent to the human SMYD3 protein by introducing an appropriate mutation in the amino acid sequence of the human SMYD3 protein using site-directed mutagenesis for example (Hashimoto-Gotoh, T. et al. (1995), Gene 152, 271-275; Zoller, M J, and Smith, M. (1983), Methods Enzymol. 100, 468-500; Kramer, W. et al. (1984), Nucleic Acids Res. 12, 9441-9456; Kramer W, and Fritz H J. (1987) Methods. Enzymol. 154, 350-367; Kunkel, T A (1985), Proc. Natl. Acad. Sci. USA. 82, 488-492). Amino acid mutations can occur in nature, too. An SMYD3 polypeptide useful in the context of the present invention includes those proteins having the amino acid sequences of the human SMYD3 protein in which one or more amino acids are mutated, provided the resulting mutated proteins are functional equivalents of the human SMYD3 protein, more particularly retain the methyltransferase activity of the human SMYD3 protein. The number of amino acids to be mutated in such a mutant is generally 20 amino acids or less, typically 10 amino acids or less, preferably 6 amino acids or less, and more preferably 3 amino acids or less. To maintain the methyltransferase activity, the SET-domains "NHSCXXN" and "GEELXXXY" are preferably conserved in the amino acid sequence of the mutated proteins ("X" indicates any amino acid). Accordingly, in the context of the present invention, the SMYD3 polypeptide includes the amino acid sequence of SEQ ID NO: 2 wherein one or more amino acids are substituted, deleted, or inserted, further wherein said polypeptide has a methyltransferase activity equivalent to that of the polypeptide having the amino acid sequence of SEQ ID NO: 2, further wherein the SET-domains "NHSCXXN" and "GEELXXXY" are conserved. More specifically, positions from 117 to amino acid 246 of the amino acid sequence of SEQ ID NO: 2 are preferably conserved.

Mutated or modified proteins, i.e., proteins having amino acid sequences modified by deleting, adding and/or replacing one or more amino acid residues of a certain amino acid sequence, are known to retain the biological activity of the original protein (Mark, D. F. et al., Proc. Natl. Acad. Sci. USA (1984) 81, 5662-5666, Zoller, M. J. & Smith, M., Nucleic Acids Research (1982) 10, 6487-6500, Wang, A. et al., Science (1984) 224, 1431-1433, Dalbadie-McFarland, G. et al., Proc. Natl. Acad. Sci. USA (1982) 79, 6409-6413). For example, the SMYD3 polypeptide is expected to retain its methyltransferase activity so long as it retains the SET-domains. Thus, the methods of the present invention can be performed using a polypeptide that comprises the amino acid sequence of positions 117 to 246 of the amino acid sequence of SEQ ID NO: 2, for example, a polypeptide comprising the amino acid sequence of positions 110 to 250 of the amino acid sequence of SEQ ID NO: 2 as shown in the Example.

The amino acid residue to be mutated is preferably mutated into a different amino acid that allows the properties of the amino acid side-chain to be conserved (a process known as conservative amino acid substitution). Examples of properties of amino acid side chains include following groups.

hydrophobic amino acids (A, I, L, M, F, P, W, Y, V),
hydrophilic amino acids (R, D, N, C, E, Q, G, H, K, S, T)

Alternatively, side chains having the following functional groups or characteristics in common:

an aliphatic side-chain (G, A, V, L, I, P);
a hydroxyl group containing side-chain (S, T, Y);
a sulfur atom containing side-chain (C, M);
a carboxylic acid and amide containing side-chain (D, N, E, Q);
a base containing side-chain (R, K, H); and
an aromatic containing side-chain (F, H, Y, W).

Further, for example, grouping of amino acids is also well known as mutational matrix (Taylor 1986, J, Theor. Biol. 119, 205-218, Sambrook, J. et al., Molecular Cloning 3rd ed. A7.6-A7.9, Cold Spring Harbor Lab. Press, 2001). Such grouping may be summarized as follows:

Aliphatic amino acids: L, I, V
Aromatic amino acids: H, W, Y, F
Charged amino acids: D, E, R, K, H
Positively charged amino acids: R, K, H
Negatively charged amino acids: D, E
Hydrophobic amino acids: H, W, Y, F, M, L, I, V, C, A, G, T, K
Polar amino acids: T, S, N, D, E, Q, R, K, H, W, Y
Small amino acids: P, V, C, A, G, T, S, N, D
Tiny amino acids: A, G, S
Large (non-small) amino acids: Q, E, R, K, H, W, Y, F, M, L, I Note, the parenthetic letters indicate the one-letter codes of amino acids.

An example of a protein in one or more amino acids residues are added to the amino acid sequence of human SMYD3 protein (SEQ ID NO: 2) is a fusion protein containing the human SMYD3 protein. Fusion proteins include fusions of the human SMYD3 protein and other peptides or proteins, and are used in the present invention. Fusion proteins can be made by techniques well known to a person skilled in the art, such as by linking the DNA encoding the human SMYD3 protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides to be fused to the SMYD3 protein include, for example, FLAG (Hopp, T. P. et al., Biotechnology (1988) 6, 1204-1210), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, alpha-tubulin fragment, B-tag, Protein C fragment, and the like. Examples of proteins that may be fused to a protein of the invention include GST (glutathione-S-transferase), Influenza agglutinin (HA), immunoglobulin constant region, beta-galactosidase, MBP (maltose-binding protein), and such.

Fusion proteins can be prepared by fusing commercially available DNA, encoding the fusion peptides or proteins discussed above, with the DNA encoding the protein of the present invention and expressing the fused DNA prepared.

An alternative method known in the art to isolate functionally equivalent proteins uses hybridization techniques to identify homologous sequences (Sambrook, J. et al., Molecular Cloning 2nd ed. 9.47-9.58, Cold Spring Harbor Lab. Press, 1989). One skilled in the art can readily isolate a DNA having high homology with a whole or part of the SMYD3 DNA sequence (e.g., SEQ ID NO: 1) encoding the human SMYD3 protein, and isolate proteins that are functionally equivalent to the human SMYD3 protein from the isolated DNA. The proteins used for the present invention include those that are encoded by DNA that hybridize with a whole or part of the DNA sequence encoding the human SMYD3 protein and that are functional equivalents of the human SMYD3 protein. These proteins include mammal homologues corresponding to the protein derived from human or mouse (for example, a protein encoded by a monkey, rat, rabbit and bovine gene). In isolating a cDNA highly homologous to the DNA encoding the human SMYD3 protein from animals, it is particularly preferable to use tissues from skeletal muscle, testis, HCC, or colorectal tumors.

The condition of hybridization for isolating a DNA encoding a functional equivalent of the human SMYD3 protein can be routinely selected by a person skilled in the art. For example, hybridization may be performed by conducting pre-hybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringency condition is, for example, 42° C., 2×SSC, 0.1% SDS, or preferably 50° C., 2×SSC, 0.1% SDS. More preferably, highly stringent conditions are used. In the context of the present invention, a highly stringent condition includes, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors such as temperature and salt concentration can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a protein that is functionally equivalent to the human SMYD3 protein, using a primer synthesized based on the sequence information of the DNA (SEQ ID NO: 1) encoding the human SMYD3 protein (SEQ ID NO: 2).

Proteins that are functional equivalents of the human SMYD3 protein, encoded by DNA isolated through the above hybridization techniques or by gene amplification techniques, normally have a high homology to the amino acid sequence of the human SMYD3 protein. "High homology" (also referred to as "high identity") typically refers to the degree of identity between two optimally aligned sequences (either polypeptide or polynucleotide sequences). Typically, high homology or identity refers to homology of 40% or higher, preferably 60% or higher, more preferably 80% or higher, even more preferably 85%, 90%, 95%, 98%, 99%, or higher. The degree of homology or identity between two polypeptide or polynucleotide sequences can be determined by following the algorithm in "Wilbur, W. J. and Lipman, D. J. Proc. Natl. Acad. Sci. USA (1983) 80, 726-730".

A protein useful in the context of the present invention may have variations in amino acid sequence, molecular weight, isoelectric point, the presence or absence of sugar chains, or form, depending on the cell or host used to produce it or the purification method utilized. Nevertheless, so long as it is a functional equivalent of human SMYD3 protein (SEQ ID NO: 2), it is useful in the present invention.

The proteins useful in the context of the present invention can be prepared as recombinant proteins or natural proteins, by methods well known to those skilled in the art. A recombinant protein can be prepared by inserting a DNA encoding a protein of the present invention (for example, the DNA corresponding to the nucleotide sequence of SEQ ID NO: 1), into an appropriate expression vector, introducing the vector into an appropriate host cell, obtaining the extract, and purifying the protein by subjecting the extract to chromatography, for example, ion exchange chromatography, reverse phase chromatography, gel filtration, or affinity chromatography utilizing a column to which antibodies against the protein of the present invention is fixed, or by combining more than one of aforementioned columns.

In addition, when a protein useful in the context of the present invention is expressed within host cells (for example, animal cells and $E.\ coli$) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin or factor-Xa as required.

A natural protein can be isolated by methods known to a person skilled in the art, for example, by contacting an affinity column, in which antibodies binding to the SMYD3 protein described below are bound, with the extract of tissues or cells expressing the protein of the present invention. The antibodies can be polyclonal antibodies or monoclonal antibodies.

In the present invention, the methyltransferase activity of an SMYD3 polypeptide can be determined by methods known in the art. For example, an SMYD3 polypeptide and a VEGFR1 peptide substrate can be incubated with a labeled methyl donor, under suitable assay conditions. Examples of preferred methyl donors include, but are not limited to, S-adenosyl-[methyl-$^{14}$C]-L-methionine, and S-adenosyl-[methyl-$^3$H]L-methionine. Transfer of the radiolabel to the VEGFR1 peptide can be detected, for example, by SDS-PAGE electrophoresis and fluorography. Alternatively, following the reaction, the VEGFR1 peptides can be separated from the methyl donor by filtration, and the amount of radio-label retained on the filter quantitated by scintillation counting. Other suitable labels that can be attached to methyl donors, such as chromogenic and fluorescent labels, and methods of detecting transfer of these labels to VEGFR1 peptides, are known in the art.

Alternatively, the methyltransferase activity of SMYD3 can be determined using an unlabeled methyl donor (e.g. S-adenosyl-L-methionine) and reagents that selectively recognize methylated VEGFR1 peptides. For example, after incubating an SMYD3, substrate to be methylated and a methyl donor under conditions suitable for methylation of the substrate, methylated substrate can be detected using conventional immunological methods. Any immunological techniques that use an antibody to recognize a methylated substrate can be used for the detection. For example, an antibody against methylated VEGFR1K831 (e.g. anti-K831me2) may be used as the antibody. Such antibodies recognizing the methylation of VEGFR1, in particular, the methylation at K831 of VEGFR1 are also provided by the present invention. ELISA or immunoblotting analysis using an antibodies recognizing methylated VEGFR1 K831 may be suitable for the present invention.

As demonstrated herein, the methylation of VEGFR1 at Lys 831 enhanced the phosphorylation of VEGFR1. Accordingly, in other embodiments, the methylation level of VEGFR1 may be estimated via phosphorylation of VEGFR1. The phosphorylation of VEGFR1 may be detected using radiolabeled phosphate donor. Alternatively, an antibody that recognizes the phosphorylation site of VEGFR1 may be used for estimating phosphorylation level of VEGFR1.

According to the invention, the above-described characteristic of the VEGFR1 peptide to be methylated by SMYD3 may be utilized for measuring the methyltransferase activity of SMYD3 and other H3K4 methyltransferases. Such methods for measuring the methyltransferase activity of a peptide comprise the steps of:

a. contacting a H3K4 methyltransferase with a VEGFR1 peptide to be methylated and a cofactor under the condition capable of methylation of the VEGFR1 peptide;

b. detecting the methylation level of the VEGFR1 peptide; and c. measuring the methyltransferase activity by correlating the methylation level of step (b) with the methyltransferase activity.

Herein, the H3K4 methyltransferase may be any polypeptide so long as it has the ability to transfer a methyl group on the VEGFR1 peptide including, but are not limited to, the aforementioned SMYD3 polypeptides. The steps of this method may be performed using the same VEGFR1 peptide, reaction conditions (addition of cofactors, enhancing agents, etc.), detection means and such as the above explained method for identifying a compound that modulates methylation of VEGFR1 by SMYD3.

The present invention further provides a method of screening for a compound for treating a cancer which over expresses SMYD3, said method including the step of identifying a test compound that modulates methylation using the method(s) described above, and selecting the test compound that decreases the methylation level of a substrate to be methylated as compared to a control methylation level detected in the absence of the test compound.

The screening may also be performed by (a) contacting a VEGFR1 peptide or fragment comprising SMYD3 binding region thereof and an SMYD3 polypeptide or fragment comprising VEGFR1 binding region thereof under a condition that allows the binding of the VEGFR1 peptide and the SMYD3 polypeptide and in the presence of a test compound; and (b) selecting the test compound that inhibits the binding between the or fragment comprising SMYD3 binding region thereof and an SMYD3 polypeptide or fragment comprising VEGFR1 binding region thereof as a candidate compound for treating cancer. In the present invention, it is revealed that suppressing the methylation of VEGFR1 by SMYD3, or binding between VEGFR1 and SMYD3, reduces cell growth. Thus, by screening for test compounds that inhibits the binding or methylation of VEGFR1 by SMYD3, candidate compounds that have the potential to treat or prevent cancers can be identified. Potential of these candidate compound to treat or prevent cancers may be evaluated by second and/or further screening to identify therapeutic agent for cancers.

In the context of the present invention, a cancer which over expresses SMYD3 includes cancers of which the expression level of SMYD3 is high compare to normal region of same organ of the cancer. For example, the present inventors have revealed over expression of SMYD3 in various cancers, e.g. colorectal cancer, hepatocellular carcinoma, bladder cancer and breast cancer (WO 2003/027143, WO 2006/085684 and WO 2006/092958). Accordingly, in preferred embodiments of the present invention, a cancer which over expresses SMYD3 may be selected from the group consisting of colorectal cancer, hepatocellular carcinoma, bladder cancer and breast cancer.

A test compound can be determined to inhibit the binding of the VEGFR1 peptide and the SMYD3 polypeptide by comparing the binding level of the VEGFR1 peptide and the SMYD3 polypeptide with that detected in the absence of the compound, and selecting a compound that reduced the binding level of the VEGFR1 peptide and the SMYD3 polypeptide. Any VEGFR1 peptide and SMYD3 polypeptide including equivalents thereof may be used for this screening so long as they retain their binding ability to each other. For instance, fragments comprising SMYD3 binding region of VEGFR1 peptide may be used as the peptide equivalent to VEGFR1. In the present invention, such peptide equivalent to VEGFR1 may comprises the amino acid sequence of positions 800-1000 of the amino acid sequence of SEQ ID NO: 4, preferably. Same way, fragments comprising VEGFR1 binding region of SMYD3 peptide may be used as the peptide equivalent to SMYD3. For example, such peptide equivalent to SMYD3 may comprises the amino acid sequence of positions 100-250 of the amino acid sequence of SEQ ID NO: 2.

In the context of the present invention, "inhibit the binding" between two proteins refers to at least reducing binding between the proteins. Thus, in some cases, the percentage of binding pairs in a sample will be decreased compared to an appropriate (e.g., not treated with test compound or from a non-cancer sample, or from a cancer sample) control. The reduction in the amount of proteins bound may be, e.g., less than 90%, 80%, 70%, 60%, 50%, 40%, 25%, 10%, 5%, 1% or less (e.g., 0%), than the pairs bound in a control sample.

Generally, any method that determines the ability of a test compound to interfere with such association is suitable for use with the present invention. For example, competitive and non-competitive inhibition assays in an ELISA format may be utilized. Control experiments should be performed to determine maximal binding capacity of system (e.g., contacting bound VEGFR1 peptide with SMYD3 polypeptide, and determining the amount of protein bound to VEGFR1 peptide, or vice versa). As a method for identifying compounds that inhibit the binding of the present invention, many methods well known by one skilled in the art can be used. Such identification can be carried out as an in vitro assay system, for example, in a cellular system. More specifically, first, either the VEGFR1 peptide or the SMYD3 polypeptide partner is bound to a support, and the other protein is contacted together with a test compound thereto. Next, the mixture is incubated, washed and the other protein bound to the support is detected and/or measured.

Example of supports that may be used for binding the proteins include insoluble polysaccharides, such as agarose, cellulose and dextran; and synthetic resins, such as polyacrylamide, polystyrene and silicon; preferably commercially available beads and plates (e.g., multi-well plates, biosensor chip, etc.) prepared from the above materials may be used. When using beads, they may be filled into a column. Alternatively, the use of magnetic beads is also known in the art, and enables to readily isolate proteins bound on the beads via magnetism.

The binding of a protein to a support may be conducted according to routine methods, such as chemical bonding and physical adsorption. Alternatively, a protein may be bound to a support via antibodies specifically recognizing the protein. Moreover, binding of a protein to a support can also be conducted by means of interacting molecules, such as the combination of avidin and biotin.

The binding between proteins is carried out in buffer, for example, but are not limited to, phosphate buffer and Tris buffer, as long as the buffer does not inhibit the binding between the proteins.

In the present invention, a biosensor using the surface plasmon resonance phenomenon may be used as a means for detecting or quantifying the bound protein. When such a biosensor is used, the interaction between the proteins can be observed real-time as a surface plasmon resonance signal, using only a minute amount of polypeptide and without labeling (for example, BIAcore, Pharmacia). Therefore, it is possible to evaluate the binding between the VEGFR1 peptide and the SMYD3 polypeptide using a biosensor such as BIAcore.

Alternatively, either the VEGFR1 peptide or the SMYD3 polypeptide may be labeled, and the label of the bound protein may be used to detect or measure the bound protein. Specifically, after pre-labeling one of the proteins, the labeled protein is contacted with the other protein in the presence of a test compound, and then bound proteins are detected or measured according to the label after washing.

Labeling substances such as radioisotope (e.g., $^{3}$H, $^{14}$C, $^{32}$P, $^{33}$P, $^{35}$S, $^{125}$I, $^{131}$I), enzymes (e.g., alkaline phosphatase, horseradish peroxidase, beta-galactosidase, beta-glucosidase), fluorescent substances (e.g., fluorescein isothiosyanete (FITC), fluorescein, Texas red, green fluorescent protein, and rhodamine), magnetic beads (e.g., DYNABEADS™), calorimetric labels (e.g., colloidal gold or colored glass or plastic (e.g., polystyrene, polypropylene, latex, etc.) beads), and biotin/avidin, may be used for the labeling of a protein in the present method. Patents teaching the use of such labels include U.S. Pat. Nos. 3,817,837; 3,850,752; 3,939,350; 3,996,345; 4,277,437; 4,275,149; and 4,366,241. However, the present invention is not restricted thereto and any label detectable by spectroscopic, photochemical, biochemical, immunochemical, electrical, optical or chemical means may be used.

When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Furthermore, the binding in the present screening method can be also detected or measured using an antibody against the VEGFR1 peptide or the SMYD3 polypeptide. For example, after contacting the VEGFR1 peptide immobilized on a support with a test compound and the SMYD3 polypeptide, the mixture is incubated and washed, and detection or measurement can be conducted using an antibody against the SMYD3 polypeptide. Alternatively, the SMYD3 polypeptide may be immobilized on a support, and an antibody against the VEGFR1 peptide may be used as the antibody.

In case of using an antibody in the present screening, the antibody is preferably labeled with one of the labeling substances mentioned above, and detected or measured based on the labeling substance. Alternatively, the antibody against the SMYD3 polypeptide or the VEGFR1 peptide may be used as a primary antibody to be detected with a secondary antibody that is labeled with a labeling substance. Furthermore, the antibody bound to the protein in the screening of the present invention may be detected or measured using protein G or protein A column.

Alternatively, in another embodiment of the identification method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 1992, 68: 597-612", "Fields and Sternglanz, Trends Genet. 1994, 10: 286-92"). In the two-hybrid system, for example, the SMYD3 polypeptide is fused to the SRF-binding region or GAL4-binding region and expressed in yeast cells. The VEGFR1 peptide is fused to the VP16 or GAL4 transcriptional activation region and also expressed in the yeast cells in the existence of a test compound. Alternatively, the VEGFR1 peptide may be fused to the SRF-binding region or GAL4-binding region, and the SMYD3 polypeptide to the VP16 or GAL4 transcriptional activation region. When the test compound does not inhibit the binding between the SMYD3 polypeptide and the VEGFR1 peptide, the binding of the two activates a reporter gene, making positive clones detectable. As a reporter gene, for example, Ade2 gene, lacZ gene, CAT gene, luciferase gene and such can be used besides HIS3 gene.

Herein, the binding level between the SMYD3 polypeptide and the VEGFR1 peptide can be also measured as any change occurring after the binding of the SMYD3 polypeptide and the VEGFR1 peptide. Specifically, such screening can be performed by contacting a test compound with a cell that expresses the SMYD3 polypeptide and the VEGFR1 peptide. For example, the suppression of cell proliferation may be detected to determine the influence of a test compound on the binding of the SMYD3 polypeptide and the VEGFR1 peptide.

1. Competitive Assay Format

Competitive assays may be used for screening test compounds of the present invention. By way of example, a competitive ELISA format may include the SMYD3 polypeptide (or the VEGFR1 peptide) bound to a solid support. The bound SMYD3 polypeptide (or the VEGFR1 peptide) would be incubated with the VEGFR1 peptide (or the SMYD3 polypeptide) and a test compound. After sufficient time to allow the test compound and/or the VEGFR1 peptide (or the SMYD3 polypeptide) to bind SMYD3 polypeptide (or the VEGFR1 peptide), the substrate would be washed to remove unbound material. The amount of the VEGFR1 peptide bound to the SMYD3 polypeptide is then determined. This may be accomplished in any of a variety of ways known in the art, for example, by using the VEGFR1 peptide (or the SMYD3 polypeptide) species tagged with a detectable label, or by contacting the washed substrate with a labeled antibody against the VEGFR1 peptide (or the SMYD3 polypeptide). The amount of the VEGFR1 peptide (or the SMYD3 polypeptide) bound to the SMYD3 polypeptide (or the VEGFR1 peptide) will be inversely proportional to the ability of the test compound to interfere with the association of the VEGFR1 peptide to the SMYD3 polypeptide. Protein, including but not limited to, antibody, labeling is described in Harlow & Lane, Antibodies, A Laboratory Manual (1988).

In a variation, the VEGFR1 peptide (or the SMYD3 polypeptide) is labeled with an affinity tag. The labeled the VEGFR1 peptide (or the SMYD3 polypeptide) is then incubated with a test compound and the SMYD3 polypeptide (or the VEGFR1 peptide), then immunoprecipitated. The immunoprecipitate is then subjected to Western blotting using an antibody against the SMYD3 polypeptide (or the VEGFR1 peptide). As with the previous competitive assay format, the amount of the SMYD3 polypeptide (or the VEGFR1 peptide) found associated with the VEGFR1 peptide (or the SMYD3 polypeptide) is inversely proportional to the ability of the test compound to interfere with the association of the VEGFR1 peptide and the SMYD3 polypeptide.

2. Non-Competitive Assay Format

Non-competitive binding assays may also find utility as an initial screen for testing agent libraries constructed in a format that is not readily amenable to screening using competitive assays, such as those described herein. An example of such a library is a phage display library (see, e.g., Barret et al., Anal Biochem 1992, 204: 357-64).

Phage libraries find utility in being able to produce quickly working quantities of large numbers of different recombinant peptides. Phage libraries do not lend themselves to competitive assays of the invention, but can be efficiently screened in a non-competitive format to determine which recombinant peptide test compounds bind to the VEGFR1 peptide or the SMYD3 polypeptide. Test compounds identified as binding can then be produced and screened using a competitive assay format. Production and screening of phage and cell display libraries is well-known in the art and discussed in, for example, Ladner et al., WO 88/06630; Fuchs et al., Biotechnology 1991, 9: 1369-72; Goward et al., TIBS1993, 18: 136-40; Charbit et al., EMBO J 1986, 5: 3029-37; Cull et al., PNAS USA 1992, 89: 1865-9; Cwirla et al., PNAS USA 1990, 87: 6378-82.

An exemplary non-competitive assay would follow an analogous procedure to the one described for the competitive assay, without the addition of one of the components (the VEGFR1 peptide or the SMYD3 polypeptide). However, as non-competitive formats determine test compounds binding to the VEGFR1 peptide or the SMYD3 polypeptide, the ability of test agent to bind both the VEGFR1 peptide and the SMYD3 polypeptide needs to be determined for each candidate. Thus, by way of example, binding of the test compound to immobilized the VEGFR1 peptide may be determined by washing away unbound test compound; eluting bound test compound from the support, followed by analysis of the eluate; e.g., by mass spectroscopy, protein determination (Bradford or Lowry assay, or Abs. at 280 nm determination). Alternatively, the elution step may be eliminated and binding of test compound determined by monitoring changes in the spectroscopic properties of the organic layer at the support surface. Methods for monitoring spectroscopic properties of surfaces include, but are not limited to, absorbance, reflectance, transmittance, birefringence, refractive index, diffraction, surface plasmon resonance, ellipsometry, resonant mirror techniques, grating coupled waveguide techniques and multipolar resonance spectroscopy, all of which are known to those of skill in the art. A labeled test compound may also be used in the assay to eliminate need for an elution step. In this instance, the amount of label associated with the support after washing away unbound material is directly proportional to test agent binding.

A number of well-known robotic systems have been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Various low-throughput and high-throughput enzyme assay formats are known in the art and can be readily adapted for detection or measuring of the methyltransferase activity of SMYD3. For high-throughput assays, the VEGFR1 peptide substrate can conveniently be immobilized on a solid support, such as a multiwell plate, slide or chip. Following the reaction, the methylated product can be detected on the solid support by the methods described above. Alternatively, the methyltransferase reaction can take place in solution, after which the VEGFR1 peptide can be immobilized on a solid support, and the methylated product detected. To facilitate such assays, the solid support can be coated with streptavidin and the VEGFR1 labeled with biotin, or the solid support can be coated with anti-VEGFR1 antibodies. The skilled person can determine suitable assay formats depending on the desired throughput capacity of the screen.

The present invention also contemplates the use of partial peptides of a protein of the present invention. A partial peptide has an amino acid sequence specific to the SMYD3 protein and preferably consists of less than about 400 amino acids, usually less than about 200 and often less than about 100 amino acids, and at least about 7 amino acids, preferably about 8 amino acids or more, and more preferably about 9 amino acids or more. The partial peptide can be used, for example, in the screening for an agent or compound that binds to the SMYD3 protein, and the screening for inhibitors of the binding between SMYD3 and a co-factor thereof, such as, for example, SAM. In the context of such screening methods, a partial peptide containing the SET-domain is preferred.

A partial peptide useful in the context of the present invention can be produced by genetic engineering, by known methods of peptide synthesis, or by digesting the protein of the invention with an appropriate peptidase. For peptide synthesis, for example, solid phase synthesis or liquid phase synthesis may be used.

An SMYD3 mutant having a mutation of SET-domain shows inhibitory effects on cell proliferation. Therefore, a partial peptide of SMYD3 preferably includes the SET-domain "NHSCXXN" and/or "GEELXXXY".

Any test agent can be used. Examples include, but are not limited to, cell extracts, cell culture supernatant, products of fermenting microorganism, extracts from marine organism, plant extracts, purified or crude proteins, peptides, non-peptide compounds, synthetic micromolecular compounds and natural compounds. The test agents or compounds of the present invention can also be obtained using combinatorial library methods known in the art, including, but not limited to, (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, Anticancer Drug Des. 12: 145-67 (1997)). Examples of methods for the synthesis of molecular libraries can be found in the art (DeWitt et al., Proc Natl Acad Sci USA. 1993 Aug. 1; 90(15):6909-13; Erb et al., Proc. Natl. Acad. Sci. USA 91: 11422-6 (1994); Zuckermann et al., J. Med. Chem. 37: 2678-85 (1994); Cho et al., Science 261: 1303-5 (1993); Carell et al., Angew. Chem. Int. Ed. Engl. 33: 2059 (1994); Carell et al., Angew. Chem. Int. Ed. Engl. 33: 2061 (1994); Gallop et al., J. Med. Chem. 37: 1233-51 (1994)). Libraries of compounds may be presented in solution (see Houghten, Bio/Techniques 13: 412-21 (1992)) or on beads (Lam, Nature 354: 82-4 (1991)), chips (Fodor, Nature 364: 555-6 (1993)), bacteria (U.S. Pat. No. 5,223,409), spores (U.S. Pat. Nos. 5,571,698; 5,403,484, and 5,223,409), plasmids (Cull et al., Proc. Natl. Acad. Sci. USA 89: 1865-9 (1992)) or phage (Scott and Smith, Science 249: 386-90 (1990); Devlin, Science 249: 404-6 (1990); Cwirla et al., Proc. Natl. Acad. Sci. USA 87: 6378-82 (1990); Felici, J. Mol. Biol. 222: 301-10 (1991); US Pat. Application 20020103360). A test compound of the present invention may be a single compound or a combination of compounds. When a combination of compounds is used in the screening methods of the invention, the compounds may be contacted sequentially or simultaneously.

Test agents or compounds useful in the assays described herein can also take the form of antibodies that specifically bind to SMYD3 or partial SMYD3 peptides that lack methyltransferase activity. For example, antibodies (e.g., monoclonal antibodies) can be tested for the ability to block the binding between SMYD3 and its VEGFR1 substrate.

An agent or compound isolated by the screening methods of the present invention is a candidate for drugs that inhibit the methyltransferase activity of SMYD3 and, thus, can be applied to the treatment or prevention of hepatocellular, colorectal, bladder and/or breast cancer.

Moreover, agents or compounds in which a part of the structure of the agent or compound inhibiting the methyltransferase activity of SMYD3 is converted by addition, deletion and/or replacement are also included in the agents and compounds obtainable by the screening methods of the present invention.

As noted above, the agents or compounds that inhibit the methyltransferase activity of SMYD3 can be either partial peptides that lack the methyltransferase activity of SMYD3 or can be antibodies against SMYD3. As used herein, the term "antibody" refers to an immunoglobulin molecule having a specific structure, that interacts (i.e., binds) only with the antigen that was used for synthesizing the antibody or with an antigen closely related thereto. Furthermore, an antibody may be a fragment of an antibody or a modified antibody, so long as it binds to the proteins encoded by SMYD3 gene. For instance, the antibody fragment may be Fab, F(ab')$_2$, Fv, or single chain Fv (scFv), in which Fv fragments from H and L chains are ligated by an appropriate linker (Huston J. S. et al. Proc. Natl. Acad. Sci. U.S.A. 85:5879-5883 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody may be modified by conjugation with a variety of molecules, such as polyethylene glycol (PEG). The present invention provides such modified antibodies. The modified antibody can be obtained by chemically modifying an antibody. Such modification methods are conventional in the field. Alternatively, an antibody may take the form of a chimeric antibody having a variable region derived from a non-human antibody and a constant region derived from a human antibody, or a humanized antibody, composed of a complementarity determining region (CDR) derived from a nonhuman antibody, a frame work region (FR) derived from a human antibody and a constant region. Such antibodies can be prepared by using conventional technologies. Humanization can be performed by substituting rodent CDRs or CDR sequences for the corresponding sequences of a human antibody (see e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies, composed of human variable regions in addition to human framework and constant regions, can also be used. Such antibodies can be produced using various techniques that are known in the art. For example, in vitro methods involving the use of recombinant libraries of human antibody fragments displayed on bacteriophage may be used (e.g., Hoogenboom & Winter, J. Mol. Biol. 227:381 (1991)). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584; 5,545,807; 5,545,806; 5,569,825; 5,625,126; 5,633,425; 5,661,016.

When administrating an agent or compound isolated by a method of the present invention as a pharmaceutical for humans and other mammals, such as mice, rats, guinea-pigs, rabbits, cats, dogs, sheep, pigs, cattle, monkeys, baboons, and chimpanzees, the isolated agent or compound can be directly administered or can be formulated into a dosage form using known pharmaceutical preparation methods. For example, according to the need, the drugs can be taken orally, as sugar-coated tablets, capsules, elixirs and microcapsules, or non-orally, in the form of injections of sterile solutions or suspensions with water or any other pharmaceutically acceptable liquid. Moreover, the agents or compounds can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; and flavoring agents such as peppermint, Gaultheria adenothrix oil and cherry. When the unit-dose form is a capsule, a liquid carrier, such as an oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80™ and HCO-50.

Sesame oil or soy-bean oil can be used as a oleaginous liquid and may be used in conjunction with benzyl benzoate or benzyl alcohol as a solubilizer and may be formulated with a buffer, such as phosphate buffer and sodium acetate buffer; a pain-killer, such as procaine hydrochloride; a stabilizer, such as benzyl alcohol and phenol; and an anti-oxidant. The prepared injection may be filled into a suitable ampoule.

Methods well known to one skilled in the art may be used to administer a pharmaceutical composition of the present invention to patients, for example as intraarterial, intravenous, or percutaneous injections and also as intranasal, intramuscular or oral administrations. The dosage and method of administration vary according to the body-weight and age of a patient and the administration method; however, one skilled in the art can routinely select a suitable method of administration. In addition, if the agent or compound of interest is encodable by a DNA, the DNA can be inserted into a vector for gene therapy and the vector administered to a patient to perform the therapy. The dosage and method of administration vary according to the body-weight, age, and symptoms of the patient but one skilled in the art can suitably select them.

For example, although the dose of an agent or compound that binds to SMYD3 and regulates its activity depends on the symptoms, a typical dose ranges from about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kg of body-weight.

The present invention further provides a method for treating cancer in a subject, such as hepatocellular carcinoma, colorectal carcinoma, bladder and breast cancer. Administration can be prophylactic or therapeutic to a subject at risk of (or susceptible to) a disorder or having a disorder associated with aberrant the methyltransferase activity of SMYD3. The method includes decreasing the function of SMYD3 in a suitable cancer cell. Function can be inhibited through the administration of an agent or compound obtained by a screening method of the present invention.

In another aspect, the present invention includes pharmaceutical, or therapeutic, compositions containing one or more therapeutic agents or compounds described herein. Alternatively, the present invention also provides use of one or more therapeutic agents or compounds described herein for manufacturing a pharmaceutical, or therapeutic, compositions for treating and/or preventing of cancer, more particularly hepatocellular carcinoma, colorectal carcinoma, bladder and breast cancer. Pharmaceutical formulations may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All such pharmacy methods include the steps of bringing into association the active compound with liquid carriers or finely divided solid carriers or both as needed and then, if necessary, shaping the product into the desired formulation.

Pharmaceutical formulations suitable for oral administration may conveniently be presented as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges that contain the active ingredient in a flavored base such as sucrose and acacia or tragacanth, and pastilles that contain the active ingredient in a base such as gelatin and glycerin or sucrose and acacia. For intra-nasal administration the compounds obtained by the invention may be used as a liquid spray or dispersible powder or in the form of drops. Drops may be formulated with an aqueous or non-aqueous base and may also include one or more dispersing agents, solubilizing agents or suspending agents. Liquid sprays are conveniently delivered from pressurized packs.

For administration by inhalation the compounds are conveniently delivered from an insufflator, nebulizer, pressurized packs or other convenient means of delivering an aerosol spray. Pressurized packs may include a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflators.

When desired, the above described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of the present invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the compositions may be administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The pharmaceutical composition preferably is administered orally or by injection (intravenous or subcutaneous), and the precise amount administered to a subject will be the responsibility of the attendant physician. However, the dose employed will depend upon a number of factors, including the age and sex of the subject, the precise disorder being treated, and its severity. Also the route of administration may vary depending upon the condition and its severity.

The present invention further provides a kit for detecting for the ability of a test compound to regulate methylation of VEGFR1, said kit including the following components:

a. an SMYD3 polypeptide having methyltransferase activity selected from the group consisting of:

i. a polypeptide having the amino acid sequence of SEQ ID NO: 2;

ii. a polypeptide having the amino acid sequence of SEQ ID NO: 2 wherein one or more amino acids are substituted, deleted, or inserted, further wherein said polypeptide has a methyltransferase activity equivalent to the polypeptide having the amino acid sequence of SEQ ID NO: 2;

iii. a polypeptide having an amino acid sequence that is at least about 80% homologous to SEQ ID NO: 2, wherein said polypeptide has a methyltransferase activity equivalent to the polypeptide having the amino acid sequence of SEQ ID NO: 2;

iv. a polypeptide encoded by a polynucleotide that hybridizes under stringent conditions to a polynucleotide having the nucleotide sequence of SEQ ID NO: 1, wherein the polypeptide has a methyltransferase activity equivalent to a polypeptide having the amino acid sequence of SEQ ID NO: 2; and v. a polypeptide that includes the amino acid sequence of positions 117 to 246 of the amino acid sequence of SEQ ID NO: 2, wherein said polypeptide has a methyltransferase activity equivalent to the polypeptide having the amino acid sequence of SEQ ID NO: 2;

b. a VEGFR1 peptide capable of being methylated by the polypeptide of (a), and c. a cofactor for the methylation of the VEGFR1 peptide.

In the present invention, preferred VEGFR1 peptides include the polypeptide composed of the amino acid sequence of SEQ ID NO: 4, or a functional mutant or fragment thereof. Preferred fragments include, but are not limited to, a polypeptide comprising or consisting of the amino acid sequence of positions 800 to 841 of the amino acid sequence of SEQ ID NO: 4, or polypeptides comprising the lysine 831 of VEGFR1. In addition, a preferred cofactor is S-adenosyl homocysteine hydrolase (SAHH). The kit of the present invention may further include a reagent for detecting methylated VEGFR1 peptide. For example, an antibody that recognizes methylated VEGFR1 peptide can be used as the detection reagent. Instructions (e.g., written, tape, VCR, CD-ROM, etc.) for carrying out the assay may also be included in the kit. The assay format of the kit is a methyltransferase assay or binding assay known in the art.

The following examples are merely illustrative and are not intended to limit the scope of the present invention. While aspects of the present invention are described in the following examples, those skilled in the art will recognize that other methods and materials similar or equivalent to those described herein can be used in the practice or testing of the present invention.

EXAMPLES

Materials and Methods

Reagents and Western Blot Analysis:

Extraction of protein, IP, and Western blot analysis were performed according to methods described in the literature (Hamamoto R et al., S Nature cell biology 2004, 6(8): 731-40). Immunoblot analysis was carried out with anti-SMYD3 (Abcam, Cambridge, Mass.), anti-HA (Sigma, St Louis, Mo.), anti-Flag (Sigma), anti-GST (B D Pharmingen, San Diego, Calif.), anti-beta-actin (Sigma), or anti-phospho-Tyrosine (PY20; Sigma) antibodies. HRP-conjugated second antibody was used for the ECL Detection System (Amersham Biosciences, Piscataway, N.J.). Recombinant histone H3 and VEGFR1 (3108) were purchased from Upstate Biotechnology (Lake Placid, N.Y.) and Calbiochem (San Diego, Calif.), respectively. Methylated lysine 831-specific antibody (anti-K831me2) was purified from the sera of rabbits immunized with RERLKLGK$^{m2}$SLGRGA, synthetic peptides containing dimethylated lysine 831.

Cell Lines and Tissue Specimens:

Human embryonic kidney cell lines (HEK293 and 293T) and a human colon cancer cell line (SW480) were obtained from the American Type Culture Collection (ATCC, Manassas, Va.). SNU423 HCC cells and MCF7 breast cancer cells were kindly provided from the Korea cell-line bank and the Cancer Institute of the Japanese Foundation for Cancer Research, respectively. All cell lines were grown in monolayers in appropriate media.

Preparation of Plasmids:

Plasmids expressing SMYD3 were prepared as described previously in the literature (Hamamoto R et al., S Nature cell biology 2004, 6(8): 731-40). The present inventors also prepared plasmids expressing HA-tagged or 3xFlag-tagged VEGFR1 by cloning various RT-PCR products containing either wild type or deleted forms of VEGFR1 into an appropriate site of pCMV-HA (Clutch, Palo Alto, Calif.), p3xFlag-CMV14 (sigma), or pGEX6P-3 vector (Amersham Biosciences). RT-PCR experiments were carried out using sets of primers (Table 1). Mutant VEGFR1 plasmids containing substitution of amino acid sequence were generated using Quickchange II XL Site-directed Mutagenesis kit according to the supplier's protocol (Strata gene, La Jolla, Calif.).

The present inventors transfected cultured cells with the mammalian plasmids using FuGENE™ 6 reagent according to the supplier's protocol (Roche, Indianapolis, Ind.). Recombinant GST-fused VEGFR1 protein was purified from *Escherichia coli*, BL21 bacterial cells using Glutathione Sepharose 4B (Amersham Biosciences). Primers used in the instant Examples are set forth below;

TABLE 1

List of primer sequences.

| primers | primer sequences | SEQ ID Nos |
| --- | --- | --- |
| GST-VEGFR1#1(F) | CGGAATTCCCCAGATGAAGTTCCTTTGGATGAG | 5 |
| GST-VEGFR1#1(R) | CCGCTCGAGAATCAGATCTTCCATAGTGATGGGCTC | 6 |
| GST-VEGFR1#2(F) | CGGAATTCGATTTCTTACAGTTTTCAAGTGGCCAG | 7 |
| GST-VEGFR1#2(R) | CCGCTCGAGAGCTGAAATACTTTCCTTGAAGAAGTC | 8 |
| GST-VEGFR1#3(F) | CGGAATTCAGCTCCGAAGTTTAATTCAGGAAGCTCT | 9 |
| GST-VEGFR1#3(R) | CCGCTCGAGCTAGATGGGTGGGGTGGAGTACAGG | 10 |
| GST-VEGFR1-N1(R) | CCGCTCGAGCACTTTTCCAAAAGCCCCTCTTCCAAG | 11 |
| GST-VEGFR1-N2(F) | CGGAATTCGGTTCAAGCATCAGCATTTGGCATTAAG | 12 |
| GST-VEGFR1-N2(R) | CCGCTCGAGCTCAGTCATCAGAGCTTTGTACTCGC | 13 |
| GST-VEGFR1-N3(F) | CGGAATTCGCTAAAAATCTTGACCCACATTGGCCAC | 14 |
| GST-VEGFR1-N3(R) | CCGCTCGAGGTAGTTGGAGAGATTTCCATATTTGCAG | 15 |
| GST-VEGFR1-N4(R) | CCGCTCGAGCTTGGTGCAGGCTCCCAGCAGG | 16 |
| VEGFR1-K819A(F) | CTCCCTTATGATGCCAGCGCGTGGGAGTTTGCCCGGGAG | 17 |
| VEGFR1-K819A(R) | CTCCCGGGCAAACTCCCACGCGCTGGCATCATAAGGGAG | 18 |
| VEGFR1-K831A(F) | GACTTAAACTGGGCGCATCACTTGGAAGAGGGGCTTTTGG | 19 |
| VEGFR1-K831A(R) | CCAAAAGCCCCTCTTCCAAGTGATGCGCCCAGTTTAAGTC | 20 |
| VEGFR1-K819E(F) | CTCCCTTATGATGCCAGCGAGTGGGAGTTTGCCCGGGAG | 21 |
| VEGFR1-K819E(R) | CTCCCGGGCAAACTCCCACTCGCTGGCATCATAAGGGAG | 22 |
| VEGFR1-K831E(F) | GACTTAAACTGGGCGAATCACTTGGAAGAGGGGCTTTTGG | 23 |
| VEGFR1-K831E(R) | CCAAAAGCCCCTCTTCCAAGTGATTCGCCCAGTTTAAGTC | 24 |
| VEGFR1-K819R(F) | CTCCCTTATGATGCCAGCCGGTGGGAGTTTGCCCGGGAG | 25 |
| VEGFR1-K819R(R) | CTCCCGGGCAAACTCCCACCGGCTGGCATCATAAGGGAG | 26 |
| VEGFR1-K831R(F) | GACTTAAACTGGGCCGATCACTTGGAAGAGGGGCTTTTGG | 27 |
| VEGFR1-K831R(R) | CCAAAAGCCCCTCTTCCAAGTGATCGGCCCAGTTTAAGTC | 28 |
| HA-VEGFR1(F) | CGGAATTCACCCAGATGAAGTTCCTTTGGATGAG | 29 |
| flag-SMYD3-wt(F) | AAGCTTGCGGCCGCGATGGAGCCGCTGAAGGTGGAAAAG | 30 |
| flag-SMYD3-wt(R) | GGTACCTCTAGATTAGGATGCTCTGATGTTGGCGTC | 31 |
| flag-VEGFR1#1(R) | GGGGTACCTCAAATCAGATCTTCCATAGTGATGGGCTC | 32 |
| flag-VEGFR1#2(R) | GGGGTACCTCAAGCTGAAATACTTTCCTTGAAGAAGTC | 33 |
| flag-VEGFR1#3(R) | GGGGTACCCTAGATGGGTGGGGTGGAGTACAGG | 34 |

TABLE 1-continued

List of primer sequences.

| primers | primer sequences | SEQ ID Nos |
|---|---|---|
| flag-SMYD3-N20 (F) | CGGAATTCCGCCGTGACCCCGCTGGCGCCCCGGAG | 35 |
| flag-SMYD3-N20 (R) | GGGGTACCTTAGGATGCTCTGATGTTGGCGTC | 36 |
| flag-SMYD3-D2(F) | CGGAATTCTGACTCCGTTCGACTTCTTGGCAG | 37 |
| flag-SMYD3-D3(F) | CGGAATTCTCGGAAGCAGCTGAGGGACCAGTACTGC | 38 |
| flag-SMYD3-SET (R) | GGGGTACCTTAGTTACCGGCGCTCCTCCTGGTC | 39 |

In Vitro Methyltransferase and Kinase Assay:

293T cells were transfected with plasmids expressing Flag-tagged wild-type SMYD3 (p3XFLAG-CMV-SMYD3). Tagged-SMYD3 protein was purified by immunoprecipitation using anti-Flag antibody. Recombinant SMYD3 protein was prepared in Sf9 cells using Baculovirus system (Invitrogen, Carlsbad, Calif.). In vitro MTase assay was performed with a slight modification as described elsewhere (Hamamoto R et al., S Nature cell biology 2004, 6(8): 731-40).

Briefly, immunoprecipitated or recombinant SMYD3 protein was mixed with 1 mcg of recombinant histone H3, or VEGFR-1 protein in the presence of 2 micro Ci of [methyl-$^3$H]-labeled S-adenosyl-L-methionine (SAM, Amersham Biosciences) as methyl donor with or without S-(5'-Adenosyl)-L-homocysteine hydrolase (SAHH; Sigma) in methyltransferase buffer (50 mM Tris-HCl pH 8.5, 100 mM NaCl, 10 mM DTT), and was incubated at 30 degrees Celsius for 1 h. Labeled protein was measured by liquid scintillation counter or detected after SDS-PAGE by fluorography. In vitro kinase assay was carried out using GST-fused VEGFR1 and HTScan™ VEGFR1 Kinase Assay Kit according to the supplier's protocol (Cell Signaling, Danvers, Mass.). Phosphorylation of the substrates was quantified by 615 nm fluorescence emission using Time-Resolved Plate Reader. (Perkin-Elmer, Wellesley, Mass.).

In Vivo Methylation Assay:

In vivo methylation of VEGFR1 was analyzed according to the method described by Liu and Dreyfuss (Liu Q and Dreyfuss G., Molecular and cellular biology 1995, 15(5): 2800-8) with slight modifications. Briefly, HEK293 cells expressing HA-tagged VEGFR1 were incubated with 100 mcg/ml of cycloheximide at 37 degrees Celsius for 30 min, and then further maintained in medium containing 10 micro Ci/ml of L-[methyl-3H]methionine for 3 h. VEGFR1 was precipitated with anti-HA antibody from the cell extract, separated by SDS-PAGE, and subsequently analyzed by BAS imaging system (BAS-TR2040, FUJI) or by immunoblot analysis.

RNA Interference:

RNAi experiments were performed with double-strand oligonucleotides of SMYD3-specific or control siRNAs that were purchased from Dharmacon (Chicago, Ill.). 1×10$^5$ of HEK293-SMYD3 cells were transfected with each siRNA at a final concentration of 100 nM using Oligofectamine. 48 h after transfection, proteins were extracted from the cells, and subjected to western blot analysis.

Statistical Analysis:

All analyses were performed using Statview software (SAS Institute, Cary, N.C.).

Example 1

SMYD3 Methylates VEGFR1 In Vitro

Recent studies have suggested that VEGFRs are involved in the human carcinogenesis. Accordingly, VEGFR1 was investigated herein as a candidate methylation target of SMYD3 using an in vitro MTase assay. The inventors prepared recombinant proteins of three cytoplasmic regions of VEGFR1 for the substrates, VEGFR1#1 (codons 800-1000), VEGFR1#2 (codons 1000-1200) and VEGFR1#3 (codons 1200-1338). SMYD3 or control protein was immunoprecipitated with anti-Flag antibody from HEK293 cells transfected with Flag-tagged SMYD3 or mock plasmids, respectively. As a result, VEGFR1#1 was significantly methylated in vitro by SMYD3 compared to control protein (FIG. 1a). However, no methylation was observed in VEGFR1#2 or VEGFR1#3, suggesting that VEGFR1#1 contained the methylated residues. Approximately three-fold higher methylation of VEGFR1#1 was detected as compared to recombinant histone H3 in vitro (data not shown).

An in vitro MTase assay was additionally carried out with recombinant SMYD3 protein purified from insect cells, the results of which corroborated methylation of VEGFR1#1, but not of VEGFR1#2 or VEGFR1#3 (FIG. 1b). To determine the methylated residue(s), the present inventors prepared additional VEGFR1 proteins containing different fragments of the VEGFR1#1 construct (FIG. 1c). In vitro MTase assay showed that VEGFR1-N1 containing codons 800-841, and VEGFR1-N7 containing codons 800-878 were methylated by SMYD3. However, no methylated bands were observed in VEGFR1-N2, N3, N4, N5, N6, or N8 containing codons 842-878, 879-920, 842-900, 879-900, 842-900, or 842-1000, respectively (FIG. 1c).

This data suggests that a region between 800 and 841 was most likely to contain methylated residue(s). Interestingly, no methylated bands were detected in VEGFR2, although its cytoplasmic regions were also analyzed as a substrate (data not shown). Taken together, the data herein further suggests that SMYD3 has both substrate and sequence specificity for methylation of non-histone protein, similar to SET7/9 and SMYD2.

Example 2

VEGFR1 Lysine 831 is Methylated by SMYD3

Most of the SET-containing methyltransferases including SMYD3 modify lysines. Accordingly, lysines within this region were investigated. It was determined that lysines 819, 828, 831, and 840, are conserved among VEGFR1 orthologues in other species (data not shown). Although an earlier report showed that K/R-S/T/A-K is a consensus methylation motif of histone methyltransferase SET7/9 (Couture J F et al., Nat Struct Mol Biol 2006, 13(2): 140-6), other target lysines of histone methyltransferases such as p53 K370, histone H3K4 and H3K27 were not flanked by K/R-S/T/A-K but S/T-K-X or X-K-S (FIG. 2a). Therefore, lysines 819 and 831 that matched these motifs and were conserved in other species were the focus of the instant assays.

An in vitro MTase assay was performed using wild type and mutant VEGFR1-N1 protein containing a substitution of the lysines to alanine (FIG. 2b). Although the assay showed methylated band in wild type and K819A mutant, K831A mutant did not demonstrate any methylated band (FIG. 2b). Additional mutant proteins in which the VEGFR1 K831 is substituted for other amino acids did not show methylation as well (FIG. 2c). To confirm the methylation of lysine 831 in vivo, methylation-specific antibody against the lysine (anti-K831me2) was prepared. In vitro MTase assay confirmed the methylated lysine 831 of recombinant VEGFR1 by fluorogram as well as western blot analysis with the anti-K831 me2 antibody (FIG. 2d).

Example 3

Methylation of Lysine 831 In Vivo

To examine methylation of VEGFR1 in vivo, an in vivo methylation assay was carried out using HEK293 cells expressing Flag-tagged SMYD3 (293-SMYD3) stably and control cells (293-Mock). The cells were transfected with HA-tagged VEGFR1, and subsequently incubated with L-[methyl-$^3$H]methionine in the presence of protein synthesis inhibitors. Immunoprecipitants of the cells with anti-HA antibody were separated by PAGE-SDS to examine the methylated VEGFR1 by fluoroimager. As expected, augmented methylation of VEGFR1 was detected in the precipitants from 293-SMYD3 cells compared to that from 293-Mock cells (FIG. 2e). Consistently, immunoblot analysis of the precipitants with anti-K831me2 antibody confirmed elevated methylation of lysine 831 compared to control cells (FIG. 2f).

To confirm the SMYD3-dependent methylation, 293-SMYD3 cells were treated with SMYD3-siRNA or control siRNAs. Immunoblot analysis with anti-SMYD3 antibody showed that SMYD3-siRNA effectively decreased expression of SMYD3 protein compared to control siRNA (FIG. 2g, upper panel). Correlated to the knockdown of SMYD3, the SMYD3-siRNA decreased methylation of K831 in the cells compared to the control siRNA (FIG. 2g, second panel), while VEGFR1 expression was almost unchanged between the siRNAs (FIG. 2g, third panel). These data suggest that lysine 831 is methylated by SMYD3 in vivo.

Example 4

Interaction Between SMYD3 and VEGFR1

Since VEGFR1 was methylated by SMYD3, the inventors investigated whether SMYD3 interacts with VEGFR1. The present inventors expressed Flag-tagged cytoplasmic regions of VEGFR1 together with HA-tagged SMYD3 in HEK293 cells. Immunoprecipitation with anti-HA antibody, and subsequent immunoblot analysis with anti-Flag antibody disclosed that SMYD3 associates with VEGFR1#1 (codons 800-1000) but not VEGFR1#2 or VEGFR1#3 (FIG. 3a). Consistently, IP with anti-Flag antibody and subsequent immunoblot analysis with anti-HA antibody corroborated the interaction between SMYD3 and VEGFR1#1 (FIG. 3a). To examine the interaction of endogenous SMYD3 with VEGFR1, the inventors additionally performed immunoprecipitation with anti-SMYD3 antibody using extracts from SNU423, SW480, or MCF7 cells that expressed both SMYD3 and VEGFR1. As a result, the inventors found that endogenous SMYD3 co-immunoprecipitates with VEGFR1 by IP with anti-SMYD3 antibody (FIG. 3b), suggesting the in vivo interaction between SMYD3 and VEGFR1. Since antibodies against VEGFR1 are not applicable for IP, the inventors did not carry out IP with the anti-VEGFR1 antibodies.

These data are consistent with the methylation of VEGFR1, because VEGFR1-#1 contains lysine 831 that is methylated by SMYD3. The present inventors also searched a responsible region of SMYD3 for the binding using plasmids expressing wild type and three deleted forms of SMYD3; SMYD3-N20 (codons 20-428), SMYD3-delta 2 (codons 100-428) and SMYD3-delta 3 (codons 250-428). Although wild type SMYD3, SMYD3-N20, and SMYD3-delta 2 interacted with VEGFR1, SMYD3-delta 3 lacking the SET domain did not (FIG. 3c). Additional plasmids expressing the SET domain (100-250) showed an association with the cytoplasmic domain of VEGFR1 (FIG. 3d). This data suggests that the SET domain is responsible for the interaction.

Example 5

Enhanced Kinase Activity of VEGFR1 Through its Methylation by SMYD3

Lysine 831 localizes within the kinase domain. Accordingly, the effect of VEGFR1 methylation on its kinase activity was further explored. The kinase activity was investigated using a VEGFR1 kinase assay kit that recognizes phosphotyrosine of the substrates. Recombinant protein of the cytoplasmic region of VEGFR1 was treated with $^3$H-labeled SAM in the presence or absence of SMYD3, and subsequently analyzed the kinase activity. As expected, methylation of VEGFR1 by SMYD3 was detected using $^3$H-BAS system (data not shown). Importantly, VEGFR1 treated with SMYD3 showed significantly increased level of kinase activity compared to that with control (FIG. 4a). No phosphorylation was observed by SMYD3 alone without VEGFR1 (data not shown). Western blot analysis with anti-phosphotyrosine antibody also revealed enhanced phosphorylation of recombinant human VEGFR1 protein fused to the Fc region with recombinant human VEGF 165 protein in the presence of SMYD3 compared to the absence of SMYD3 (FIG. 4b). Interestingly, autophosphorylation of VEGFR1 was not observed when recombinant cytoplasmic region of VEGFR1 (codons 784-1338) was used in the in vitro kinase assay (data not shown). Therefore methylation of VEGFR1 may affect the phosphorylation of VEGFR1-target molecules resulting in its enhanced signaling.

DISCUSSION

As demonstrated herein, VEGFR1 is a novel non-histone target of SMYD3 histone methyltransferase. Modification of histone tails plays crucial roles in transcription, DNA repair, telomere maintenance, DNA replication, and chromosome segregation through in part alteration of chromatin structure. Recent molecular studies have disclosed the importance of lysine modifications in histone tails, and its dynamic regulation by histone methyltransferases and demethylases (Volkel P and Angrand P O, Biochimie 2007, 89(1): 1-20). More than 17 histone methyltransferases have been identified so far, and these methyltransferases have specificity for their substrate. H3K4 is mono-di- or tri-methylated by SET7/9, Set1, MLL1, MLL2, MLL3, MLL4, MLL5, ASH1 and SMYD3 (Kouzarides T, Cell 2007, 128(4): 693-705; Volkel P and Angrand P O, Biochimie 2007, 89(1): 1-20).

Importantly, among these methyltransferases, SET7/9 and SMYD2 have been shown to methylate non-histone proteins (Kouskouti A et al., Mol Cell 2004, 14(2): 175-82; Chuikov S et al., Nature 2004, 432(7015): 353-60; Huang J et al., Nature 2006, 444(7119): 629-32). SET7/9 methylated lysine 372 in p53 in vitro and in vivo, which increased the stability of p53 (Chuikov S et al., Nature 2004, 432(7015): 353-60). SET7/9 also showed methyltransferase activity on lysine-189 of TAF10 (Kouskouti A et al., Mol Cell 2004, 14(2): 175-82) and lysine 5 of TAF7 (human TATA box-binding protein-associated factors) (Couture J F et al., Nat Struct Mol Biol 2006, 13(2): 140-6).

In addition, methylation of p53 K370 has been demonstrated by SMYD2, another member of the SMYD3 (SET and MYND domain) family (Huang J et al., Nature 2006, 444 (7119): 629-32). Herein, it is confirmed that VEGFR1 is a novel non-histone target of an H3K4 histone methyltransferase that is localized in cytoplasm and nucleus. Since other H3K4 methyltransferases, such as Set1, MLL1, MLL2, MLL3, MLL4, MLL5, and ASH1, should recognize the same histone lysine modification, it will be interesting to see how substrates are modified by different methyltransferases. Since histone methylation is dynamically regulated, methylation of non-histone protein may be also modulated by histone demethylases. Accordingly, it is expected that the methylated lysine 831 in VEGFR will be catalyzed by H3K4 demethylases such as LSD1 (Shi Y et al., Cell 2004, 119(7): 941-53) and JARID1 (Seward D J et al., Nat Struct Mol Biol 2007, 14(3): 240-2).

VEGFRs are receptor tyrosine kinases (RTKs) composed of an extracellular ligand-binding domain, a transmembrane domain, a kinase domain, and a carboxyl-terminal region. All RTKs including VEGFR1 contain an evolutionary conserved kinase domain containing GXGXXG, ATP binding site, HRDLA, a motif essential for catalysis, and one or two tyrosine autophosphorylation sites (Rahimi N, Experimental eye research 2006, 83(5): 1005-16; Shibuya M, Journal of biochemistry and molecular biology 2006, 39(5): 469-78).

As demonstrated herein, SMYD3 induced methylation of lysine 831 results in an enhanced kinase activity of VEGFR-1 in vitro. Although not wishing to be bound by theory, it is believed that this result stems from the fact that the lysine residue is located three amino-acid N-terminal from "GXGXXG" motif in the kinase domain. Thus, methylation of lysine 831 may alter conformation of the kinase domain. Alternatively, methylation of VEGFR1 may suppress the inhibitory domain to increase the kinase activity since the C-terminal region of the cytoplasmic domain of VEGFR1 has an inhibitory role for the kinase activity (Shibuya M, Journal of biochemistry and molecular biology 2006, 39(5): 469-78).

Recent studies on histone tails have evidenced that their modified residues are recognized by specific molecules; phosphorylated H3S10 recruits GCN5, PVAF, and p300, methylated H3K9 recruits heterochromatin protein 1 (HP1), and methylated H3K4 recruits CHD1, SNF2L/ISWI, WDR5, BPTF/NURF301, and ING2. Therefore, methylated lysine 831 may recruit methylation-specific protein complex(es) that may affect the kinase activity to VEGFR1. Modification of a histone tail is associated with modifications in other histone tails, indicating the interplay between covalent modifications (Strahl B D and Allis C D, Nature 2000, 403(6765): 41-5; Jenuwein T and Allis C D, Science 2001, 293(5532): 1074-80; Li B et al., Cell 2007, 128(4): 707-19; Zhang Y and Reinberg D, Genes & development 2001, 15(18): 2343-60).

Phosphorylation of H3S10 facilitates GCN5-mediated acetylation of H3K14, but inhibits methylation of H3K9 by SUV39H1. On the contrary, methylation of H3K9 suppresses phosphorylation of H3S10. Similarly, methylation of H4K3 facilitates acetylation of H4K8 and H4K12 (Zhang Y and Reinberg D, Genes & development 2001, 15(18): 2343-60). The view of interplay between covalent histone modifications is tempting us to speculate that methylation of VEGFR1 may alter its autophosphorylation by its enhanced kinase activity and subsequent phosphorylation of VEGFR2 through the intermolecular phosphorylation. Although the methylated lysine 831 seems to be far from Try1169, 1213, 1242, 1327, and 1333, the phosphorylated tyrosines in VEGFR1 (Olsson A K et al., Nature reviews 2006, 7(5): 359-71), these residues may show a structurally close localization to lysine 831. In addition, future studies on the VEGF signaling by different ligands may lead to the better understanding of the role of VEGFR1 methylation.

Earlier studies reported that the recognition motif (K/R-S/T/A-K) is the consensus recognition site for SET7/9 methyltransferase (Couture J F et al., Nat Struct Mol Biol 2006, 13(2): 140-6). However, the flanking sequences of methylated lysines by other histone methyltransferases do not always agree with this motif. Comparison of the amino-acid sequences of histone H3K9, H3K27, and lysine 370 of p53 has found that X-K-S is another conserved motif of histone lysine methyltransferase. Importantly, the methylated lysine 831 in VEGFR1 is in good agreement with this notion. Although the kinase domain of VEGFR2 shared 70.1% amino acid similarity with that of VEGFR1, VEGFR2 was not methylated by SMYD3. This result is compatible with the conserved motifs, because the corresponding lysine to lysine 831 in VEGFR2 was not flanked by the consensus sequences. It is interesting to note that the VEGFR2 that showed high kinase activity as compared to VEGFR1 was not methylated by SMYD3.

Although SMYD3 may not affect the methylation of VEGFR2, it may affect phosphorylation of VEGFR2 through the phosphorylation of VEGFR1, because these two molecules form a heterodimer (Rahimi N, Experimental eye research 2006, 83(5): 1005-16; Shibuya M, Journal of biochemistry and molecular biology 2006, 39(5): 469-78). It is well known that phosphorylation of one receptor affects phosphorylation of the other receptor by intramolecular phosphorylation (Shibuya M, Journal of biochemistry and molecular biology 2006, 39(5): 469-78). It is additionally of note that yeast Rkm1, a SET domain-containing enzyme, revealed methyltransferase activity to Rpl23a and Rpl23b (Porras-Yakushi T R et al., J Biol Chem 2007, 282(17):12368-76). The comparison of the target sequences around the methylated lysines suggested that N/P-P-K might be a target for the methylation. Therefore the flanking sequence of lysine may be different among methyltransferases.

Although VEGFR1 had been believed to be expressed exclusively on vascular endothelial cells, recent studies have shown VEGFR1 expression in non-EC cells. VEGFR1 is expressed in a wide range of human tissues including colon (Lesslie D P et al., Br J Cancer 2006, 94(11): 1710-7; Fan F et al., Oncogene 2005, 24(16): 2647-53; Duff S E et al., Eur J Cancer 2006, 42(1): 112-7; Andre T et al., International journal of cancer 2000, 86(2): 174-81), breast (Li Y S et al., Pathology international 2006, 56(5): 256-61; Wu Y et al., International journal of cancer 2006, 119(7): 1519-29), pancreatic (Chung G G et al., Cancer 2006, 106(8): 1677-84; Yang A D et al., Cancer Res 2006, 66(1): 46-51), prostate (Jackson M W et al., Cancer Res 2002, 62(3): 854-9), renal (Jacobsen J et al., BJU Int 2006, 97(5): 1102-8; Ljungberg B J et al., BJU Int 2006, 98(3): 661-7) and ovarian (Wang F Q et al., International journal of cancer 2006, 118(4): 879-88; Chen H et al., Gynecol Oncol 2004, 94(3): 630-5) cancer tissues and cancer cell lines (Fan F et al., Oncogene 2005, 24(16): 2647-53; Duff S E et al., Eur J Cancer 2006, 42(1): 112-7; Wu Y et al., International journal of cancer 2006, 119(7): 1519-29; Jackson M W et al., Cancer Res 2002, 62(3): 854-9; Soker S et al., Am J Pathol 2001, 159(2): 651-9; Wu W et al., Oncogene 2003, 22(22): 3361-70). Reportedly, VEGFR1 expression was faint in primary colon cancer specimen, but its expression was clearly detected in liver metastasis (Fan F et al., Oncogene 2005, 24(16): 2647-53).

Furthermore, it was reported that VEGFR1 is implicated in tumor growth and progression; exogenous expression of VEGFR1 enhanced migration and invasion of pancreatic cancer cells. Hence, enhanced expression of SMYD3 may render invasive and/or metastasizing property to cancer cells. In this context, therapeutic approaches targeting VEGFR1 methylation may benefit patients by inhibiting invasion and metastasis of cancer cells. Suppression of the methyltransferase activity of SMYD3 may help the inhibition of VEGFR1 mediated cancer progression.

As disclosed herein, SMYD3 methylates lysine 831 of VEGFR1 in vitro and in vivo, and methylated VEGFR1 has augmented its kinase activity compared to unmethylated VEGFR1. Therefore, cancer cells expressing abundant SMYD3 protein may show enhanced signal transduction pathway mediated by VEGFR1. This data may shed light on the novel regulatory mechanism of VEGFR1 and the deregulated VEGFR1 signaling that is involved in human carcinogenesis.

INDUSTRIAL APPLICABILITY

The present invention is useful in the identification of additional molecular targets for prevention, diagnosis and treatment of various cancers, including colorectal cancer, hepatocellular carcinoma, bladder cancer and breast cancer. Furthermore, the data reported herein add to a comprehensive understanding of cancer, facilitate development of novel diagnostic strategies, and provide clues for identification of molecular targets for therapeutic drugs and preventative agents. Such information contributes to a more profound understanding of tumorigenesis, and provides indicators for developing novel strategies for diagnosis, treatment, and ultimately prevention of cancer.

While the present invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. A method for identifying an agent that modulates methylation of VEGFR1 by SMYD3, said method comprising the steps of:
   a. contacting an SMYD3 polypeptide having a methyltransferase activity selected from the group consisting of:
      i. a polypeptide comprising the amino acid sequence of SEQ ID NO: 2; and
      ii. a polypeptide that comprises the amino acid sequence having at least 95% identity to SEQ ID NO: 2, wherein said polypeptide comprises the amino acid sequence of positions 100-250 of the amino acid sequence of SEQ ID NO: 2, and has a methyltransferase activity equivalent to the polypeptide consisting of the amino acid sequence of SEQ ID NO:2;
   with a VEGFR1 peptide to be methylated and a cofactor in the presence of the agent under conditions suitable for methylation of the VEGFR1 peptide, wherein said VEGFR1 peptide is selected from the group consisting of
      I. a VEGFR1 polypeptide comprising the amino acid sequence SEQ ID NO: 4;
      II. polypeptide fragment of I, wherein said fragment comprises the amino acid sequence of positions 800-1000; and
      III. VEGFR1 mutant, wherein said mutant comprises the amino acid sequence of SEQ ID NO:4 including any one of the following mutations: K819A, K819E and K819R;
   b. detecting the methylation level of the VEGFR1 peptide; and
   c. comparing the methylation level of step (b) with a control level detected in the absence of the agent, wherein an increase or decrease in the methylation level compared to the control level indicates that the agent modulates the methylation of VEGFR1 by SMYD3.

2. The method of claim 1, wherein said cofactor is S-adenosyl-L-methionine (SAM).

3. The method of claim 1, wherein the methylation level is detected at VEGFR1 lysine 831.

* * * * *

UNITED STATES PATENT AND TRADEMARK OFFICE
CERTIFICATE OF CORRECTION

PATENT NO.       : 8,354,223 B2                                                                Page 1 of 1
APPLICATION NO. : 12/664378
DATED            : January 15, 2013
INVENTOR(S)      : Nakamura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this
First Day of September, 2015

Michelle K. Lee
*Director of the United States Patent and Trademark Office*